(12) United States Patent
Ho et al.

(10) Patent No.: US 11,577,191 B1
(45) Date of Patent: Feb. 14, 2023

(54) PORTABLE PRESSURE SWING ADSORPTION METHOD AND SYSTEM FOR FUEL GAS CONDITIONING

(71) Applicant: Coldstream Energy IP, LLC, Dallas, TX (US)

(72) Inventors: Jason G. S. Ho, Houston, TX (US); Gerald Bowen Gump, Allen, TX (US); Pedro T. Santos, Houston, TX (US); Xuepei Yuan, Humble, TX (US)

(73) Assignee: Coldstream Energy IP, LLC, Dallas, TX (US)

( * ) Notice: Subject to any disclaimer, the term of this patent is extended or adjusted under 35 U.S.C. 154(b) by 0 days.

(21) Appl. No.: 17/940,736

(22) Filed: Sep. 8, 2022

Related U.S. Application Data

(60) Provisional application No. 63/323,628, filed on Mar. 25, 2022, provisional application No. 63/242,396, filed on Sep. 9, 2021.

(51) Int. Cl.
*B01D 53/047* (2006.01)
*B01D 53/053* (2006.01)
(Continued)

(52) U.S. Cl.
CPC ......... *B01D 53/053* (2013.01); *B01D 53/047* (2013.01); *B01D 53/0438* (2013.01);
(Continued)

(58) Field of Classification Search
CPC .. B01D 53/04; B01D 53/047; B01D 53/0438; B01D 53/0446; B01D 53/053;
(Continued)

(56) References Cited

U.S. PATENT DOCUMENTS

| 2,978,063 A | 4/1961 | Ford et al. |
| 4,857,078 A | 8/1989 | Watler |
| (Continued) | | |

FOREIGN PATENT DOCUMENTS

| BR | 202016025797 | 5/2018 |
| CA | 2450485 A1 | 11/2003 |
| (Continued) | | |

OTHER PUBLICATIONS

International Searching Authority (ISA/KR), International Search Report for PCT/US2022/042929, dated Dec. 27, 2022, 3 pages.
(Continued)

*Primary Examiner* — Frank M Lawrence, Jr.
(74) *Attorney, Agent, or Firm* — Frederic Dorwart, Lawyer PLLC; Penina Michlin Chiu

(57) ABSTRACT

A portable pressure swing adsorption method and system for fuel gas conditioning. A fuel gas conditioning system includes a pressure swing adsorption (PSA) system fluidly coupled to a rich gas stream, the PSA system including a plurality of adsorbent beds and configured to condition the rich natural gas stream and produce therefrom a high-quality fuel gas and gaseous separated heavier hydrocarbons, a product end of the adsorbent beds fluidly coupled to a fuel gas line, wherein the high-quality fuel gas is discharged from the product end and supplied to the fuel gas line, and a feed end of the adsorbent beds configured to be fluidly coupled to the rich natural gas stream or a raw natural gas stream, wherein the produced gaseous separated heavier hydrocarbons are recirculated into the rich natural gas stream or the raw natural gas stream.

10 Claims, 17 Drawing Sheets

(51) Int. Cl.
*B01D 53/04* (2006.01)
*C07C 7/12* (2006.01)

(52) U.S. Cl.
CPC ............ *B01D 53/0446* (2013.01); *C07C 7/12* (2013.01); *B01D 2256/245* (2013.01); *B01D 2257/702* (2013.01); *B01D 2259/404* (2013.01); *B01D 2259/40086* (2013.01); *B01D 2259/4541* (2013.01)

(58) Field of Classification Search
CPC ........ B01D 2256/245; B01D 2257/702; B01D 2259/40086; B01D 2259/404; B01D 2259/4541; C07C 7/12; C07C 7/13
USPC .............................................. 95/96; 585/820
See application file for complete search history.

(56) References Cited

U.S. PATENT DOCUMENTS

| | | | |
|---|---|---|---|
| 5,171,333 | A | 12/1992 | Maurer |
| 5,536,300 | A * | 7/1996 | Reinhold, III ........... C10G 5/02 95/143 |
| 6,047,747 | A | 4/2000 | Bowen et al. |
| 6,989,103 | B2 | 1/2006 | Mohsen et al. |
| 7,108,070 | B2 | 9/2006 | Hall et al. |
| 7,520,916 | B2 | 4/2009 | Mcelroy et al. |
| 7,644,676 | B2 | 1/2010 | Lee et al. |
| 7,914,749 | B2 | 3/2011 | Carstens et al. |
| 7,947,118 | B2 | 5/2011 | Rarig et al. |
| 8,394,174 | B2 | 3/2013 | Chen et al. |
| 8,739,569 | B2 | 6/2014 | Oka et al. |
| 9,034,079 | B2 | 5/2015 | Deckman et al. |
| 9,174,707 | B2 | 11/2015 | Jang et al. |
| 9,187,996 | B1 | 11/2015 | Nevison et al. |
| 9,382,115 | B2 | 7/2016 | Bowe et al. |
| 9,387,430 | B2 | 7/2016 | Ho et al. |
| 9,579,598 | B2 | 2/2017 | Ritter et al. |
| 9,598,946 | B2 | 3/2017 | Shomody et al. |
| 9,631,865 | B1 | 4/2017 | Alvarez |
| 9,771,522 | B2 | 4/2017 | Matteucci et al. |
| 9,719,024 | B2 | 8/2017 | Young et al. |
| 9,835,373 | B2 | 12/2017 | Davies et al. |
| 9,856,197 | B2 | 1/2018 | Zubrin et al. |
| 9,863,581 | B2 | 1/2018 | Santos et al. |
| 9,908,078 | B2 | 3/2018 | Ho et al. |
| 9,944,872 | B2 | 4/2018 | Matteucci et al. |
| 9,945,608 | B2 | 4/2018 | Ploeger et al. |
| 9,976,091 | B2 | 5/2018 | Matteucci et al. |
| 9,982,516 | B2 | 5/2018 | Ricotta |
| 10,000,704 | B2 | 6/2018 | Young et al. |
| 10,012,062 | B2 | 7/2018 | Gupta et al. |
| 10,017,701 | B2 | 7/2018 | Meyer |
| 10,030,815 | B2 | 7/2018 | Fuchs et al. |
| 10,247,359 | B2 | 4/2019 | Tseng et al. |
| 10,263,265 | B2 | 4/2019 | Andrzejak et al. |
| 10,293,298 | B2 | 5/2019 | Marshall et al. |
| 10,308,326 | B2 | 6/2019 | Oh et al. |
| 10,441,915 | B2 | 10/2019 | Ho et al. |
| 10,487,984 | B2 | 11/2019 | Oh et al. |
| 10,537,844 | B2 | 1/2020 | Marshall et al. |
| 10,646,817 | B2 | 5/2020 | Ho et al. |
| 10,730,005 | B2 | 8/2020 | Ho et al. |
| 10,738,254 | B2 | 8/2020 | Lokhandwala et al. |
| 11,117,088 | B2 | 9/2021 | Boulet et al. |
| 2002/0002318 | A1 | 1/2002 | O'Rear et al. |
| 2008/0127673 | A1 | 6/2008 | Bowen et al. |
| 2008/0190290 | A1 * | 8/2008 | Reinhold ............. B01D 53/047 95/98 |
| 2010/0038907 | A1 | 2/2010 | Hunt et al. |
| 2010/0205979 | A1 | 8/2010 | Gentry et al. |
| 2011/0067439 | A1 | 3/2011 | Bridgwood |
| 2011/0272151 | A1 | 11/2011 | Matzakos |
| 2013/0186132 | A1 | 7/2013 | Banszky |
| 2013/0206581 | A1 * | 8/2013 | Kim ....................... B01D 53/04 203/41 |
| 2013/0213085 | A1 | 8/2013 | Ward |
| 2013/0298572 | A1 | 11/2013 | Mak |
| 2014/0310049 | A1 | 10/2014 | Goel et al. |
| 2014/0366577 | A1 | 12/2014 | Zubrin et al. |
| 2015/0299596 | A1 | 10/2015 | Sethna et al. |
| 2015/0324714 | A1 | 11/2015 | Shao et al. |
| 2015/0376092 | A1 | 12/2015 | Tsai et al. |
| 2016/0178127 | A1 | 6/2016 | Oh et al. |
| 2016/0216030 | A1 | 7/2016 | Truong et al. |
| 2016/0230519 | A1 | 8/2016 | Leniek, Sr. et al. |
| 2016/0340595 | A1 | 11/2016 | Matteucci et al. |
| 2016/0369611 | A1 | 12/2016 | Bragg |
| 2018/0045460 | A1 | 2/2018 | Zubrin et al. |
| 2018/0259248 | A1 | 9/2018 | Repasky |
| 2018/0265769 | A1 | 9/2018 | Nevison |
| 2019/0041004 | A1 | 2/2019 | Krueger et al. |
| 2019/0193818 | A1 | 6/2019 | Oh et al. |
| 2019/0249828 | A1 | 8/2019 | Subreville et al. |
| 2019/0351365 | A1 | 11/2019 | Ho et al. |
| 2020/0002628 | A1 | 1/2020 | Dugas et al. |
| 2020/0087591 | A1 | 3/2020 | Cavness et al. |
| 2020/0190925 | A1 | 6/2020 | Shuck |
| 2020/0247440 | A1 | 8/2020 | Yuki et al. |

FOREIGN PATENT DOCUMENTS

| | | |
|---|---|---|
| CN | 1019139 B | 11/1992 |
| CN | 1091459 A | 8/1994 |
| CN | 2571762 A1 | 9/2003 |
| CN | 101575532 B1 | 4/2013 |
| CN | 202868303 A | 4/2013 |
| CN | 103540335 A1 | 1/2014 |
| CN | 105627694 B | 6/2016 |
| CN | 106764410 A | 5/2017 |
| CN | 207091357 A1 | 3/2018 |
| CN | 106838605 B | 9/2018 |
| CN | 108960699 A | 12/2018 |
| CN | 109404079 A | 3/2019 |
| CN | 109472475 A | 3/2019 |
| CN | 107366829 B | 8/2019 |
| CN | 107461601 B | 10/2019 |
| CN | 111188992 A | 5/2020 |
| EP | 2442056 A2 | 4/2012 |
| EP | 1715240 B1 | 7/2019 |
| EP | 3514466 A2 | 7/2019 |
| EP | 3428053 B1 | 2/2020 |
| GB | 2348437 A1 | 10/2000 |
| GB | 2450565 A1 | 12/2008 |
| IN | 229DE2012 A | 6/2015 |
| JP | 2007085403 A | 4/2007 |
| JP | 2014122284 A1 | 7/2014 |
| KR | 100536766 | 12/2005 |
| KR | 20140056844 A | 5/2014 |
| KR | 20160091784 A | 8/2016 |
| KR | 20160091785 A | 8/2016 |
| KR | 101707515 B1 | 2/2017 |
| KR | 20180046102 A | 5/2018 |
| RU | 2688151 C1 | 5/2019 |
| RU | 2705160 C1 | 11/2019 |
| RU | 2714486 C1 | 2/2020 |
| RU | 2718073 C1 | 3/2020 |
| RU | 2727503 C1 | 7/2020 |
| WO | 2015123257 | 8/2015 |
| WO | 2017184708 A1 | 10/2017 |
| WO | 2018085076 A1 | 5/2018 |
| WO | 2019009745 A1 | 1/2019 |
| WO | 2019095031 A1 | 5/2019 |

OTHER PUBLICATIONS

International Searching Authority (ISA/KR), Written Opinion of the International Searching Authority for PCT/US2022/042929, dated Dec. 27, 2022, 5 pages.

* cited by examiner

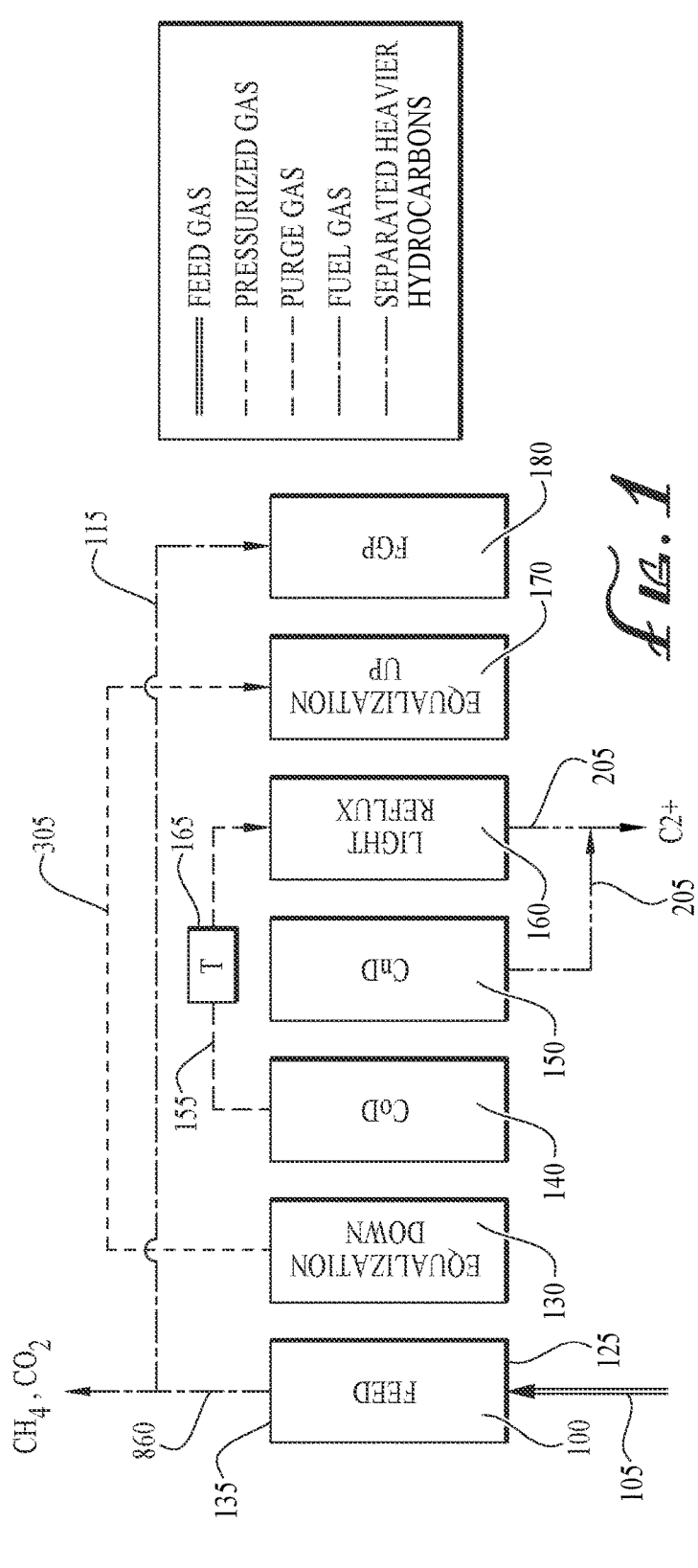

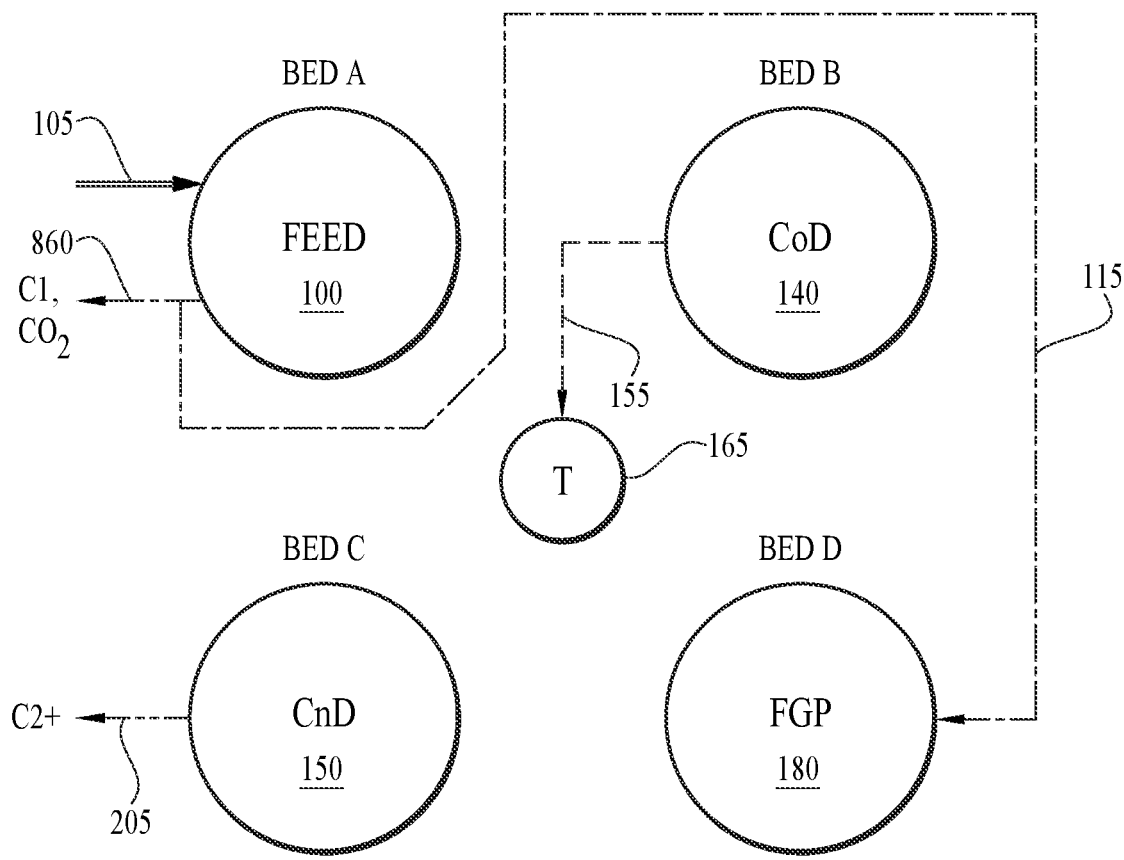
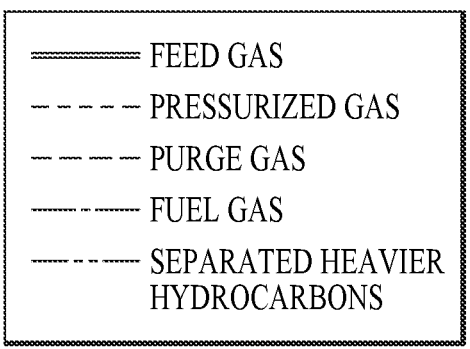

TIME INCREMENT 3
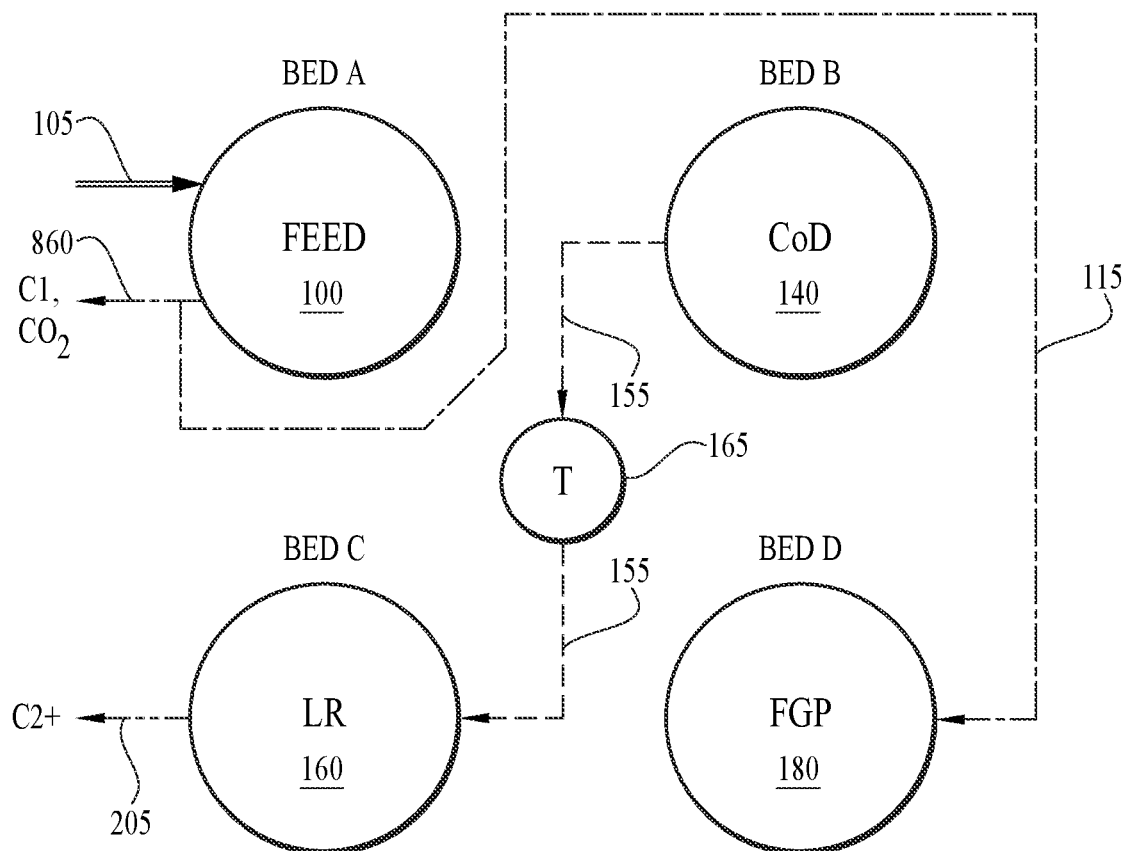
FIG. 3C
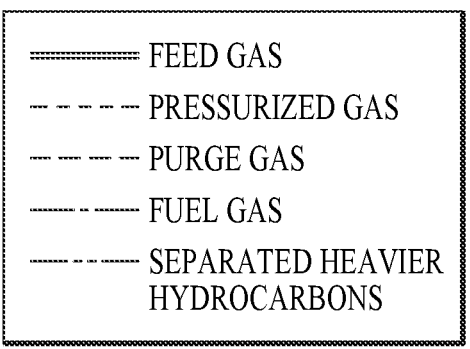

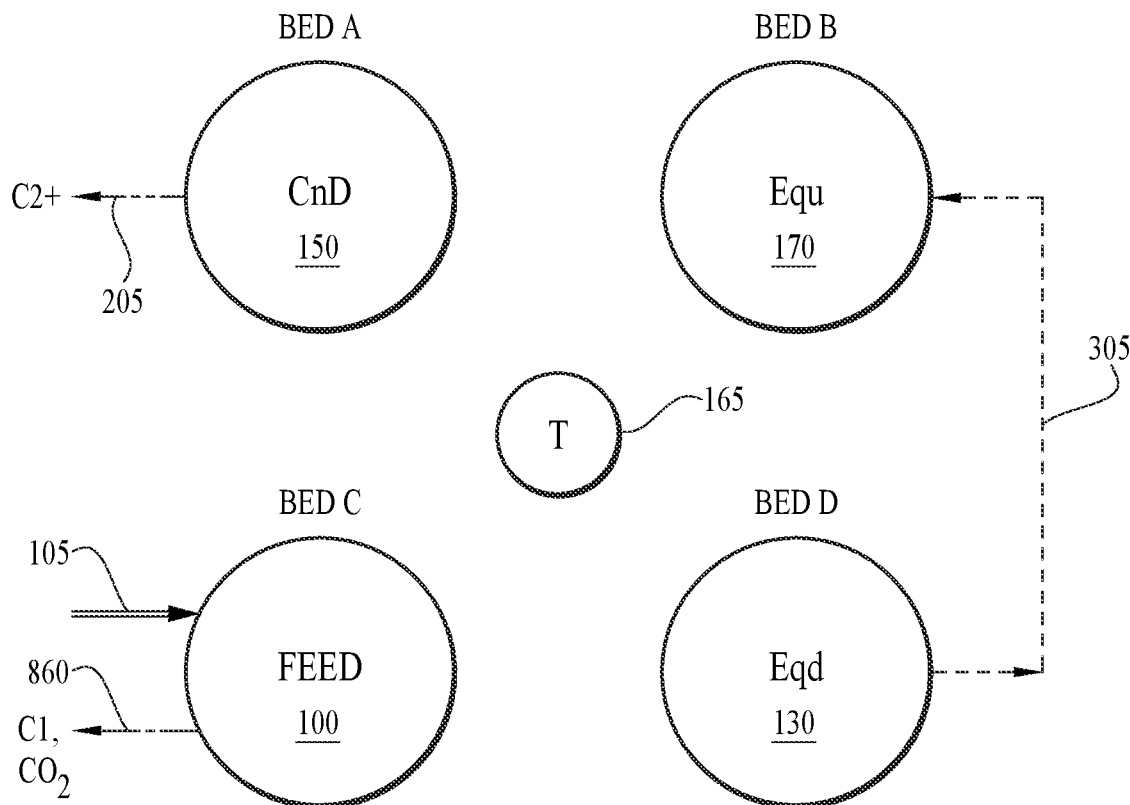
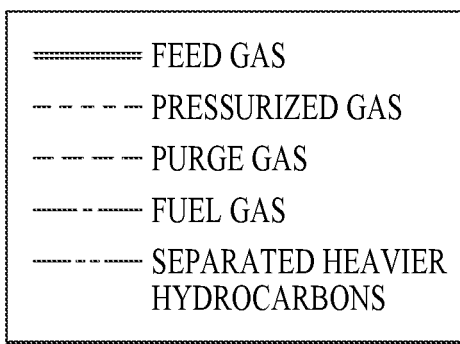

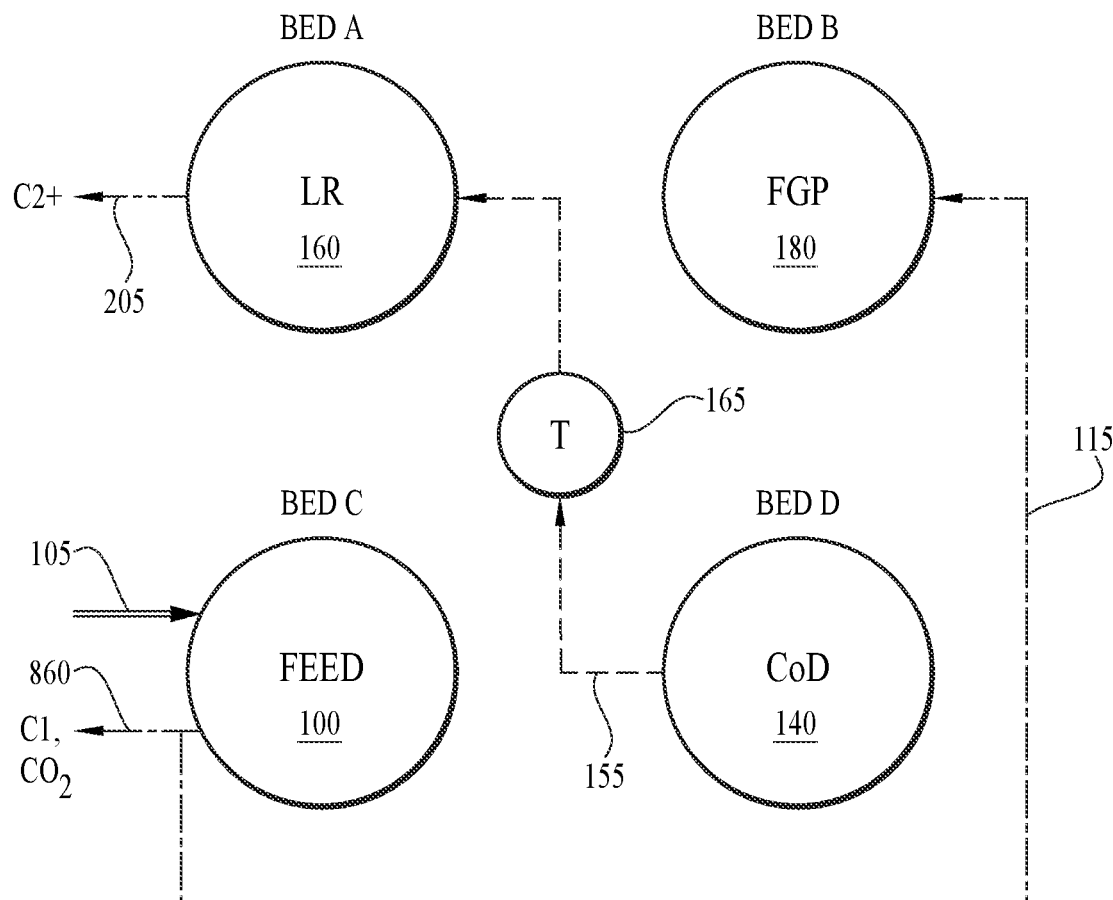
TIME INCREMENT 9
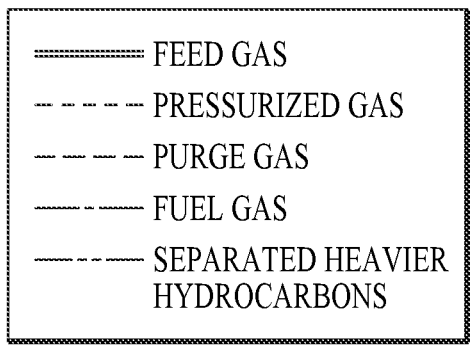
FIG. 3I

TIME INCREMENT 10
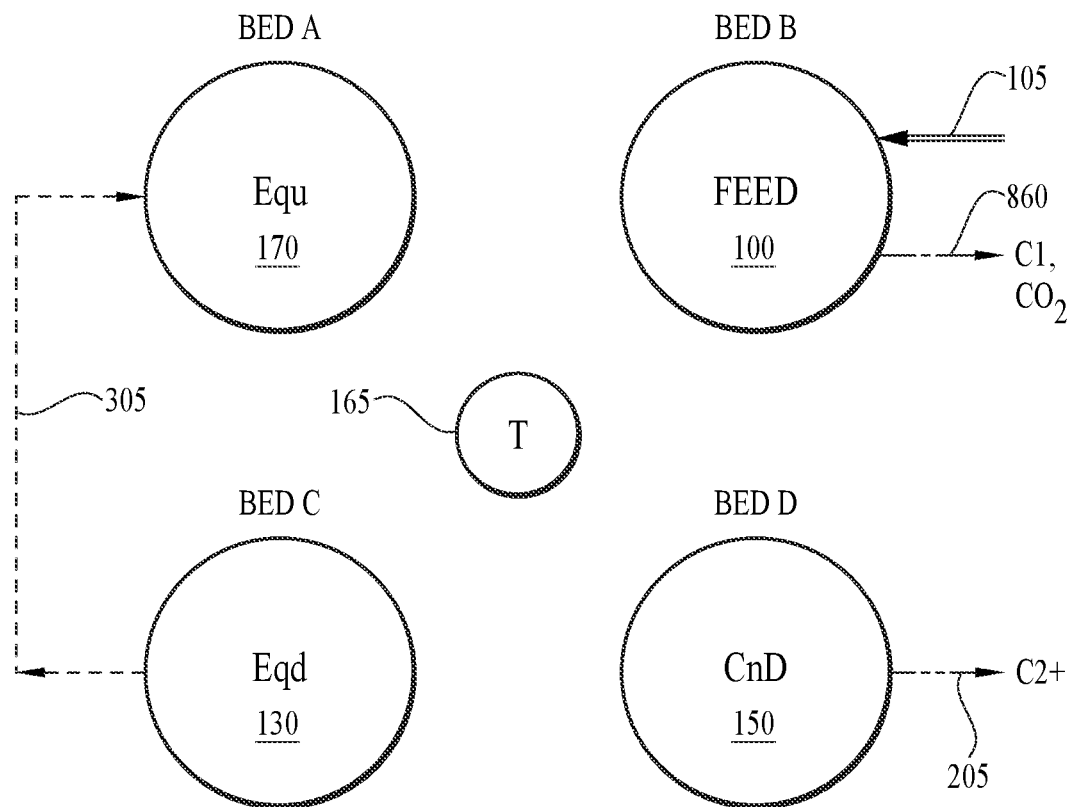
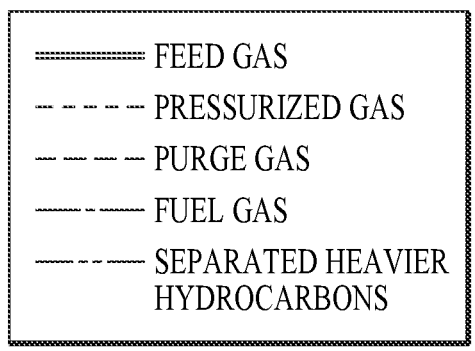
FIG. 3J

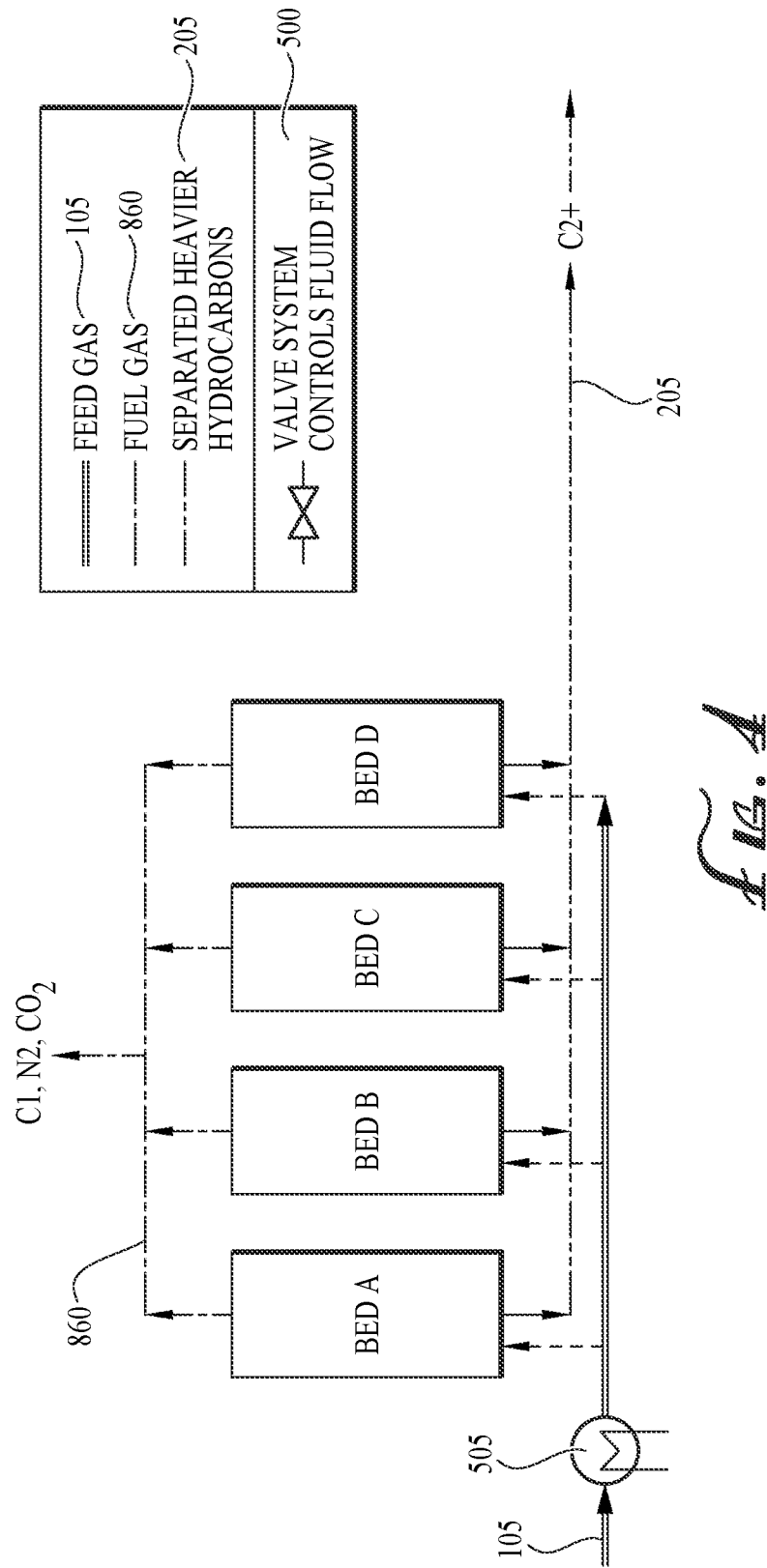

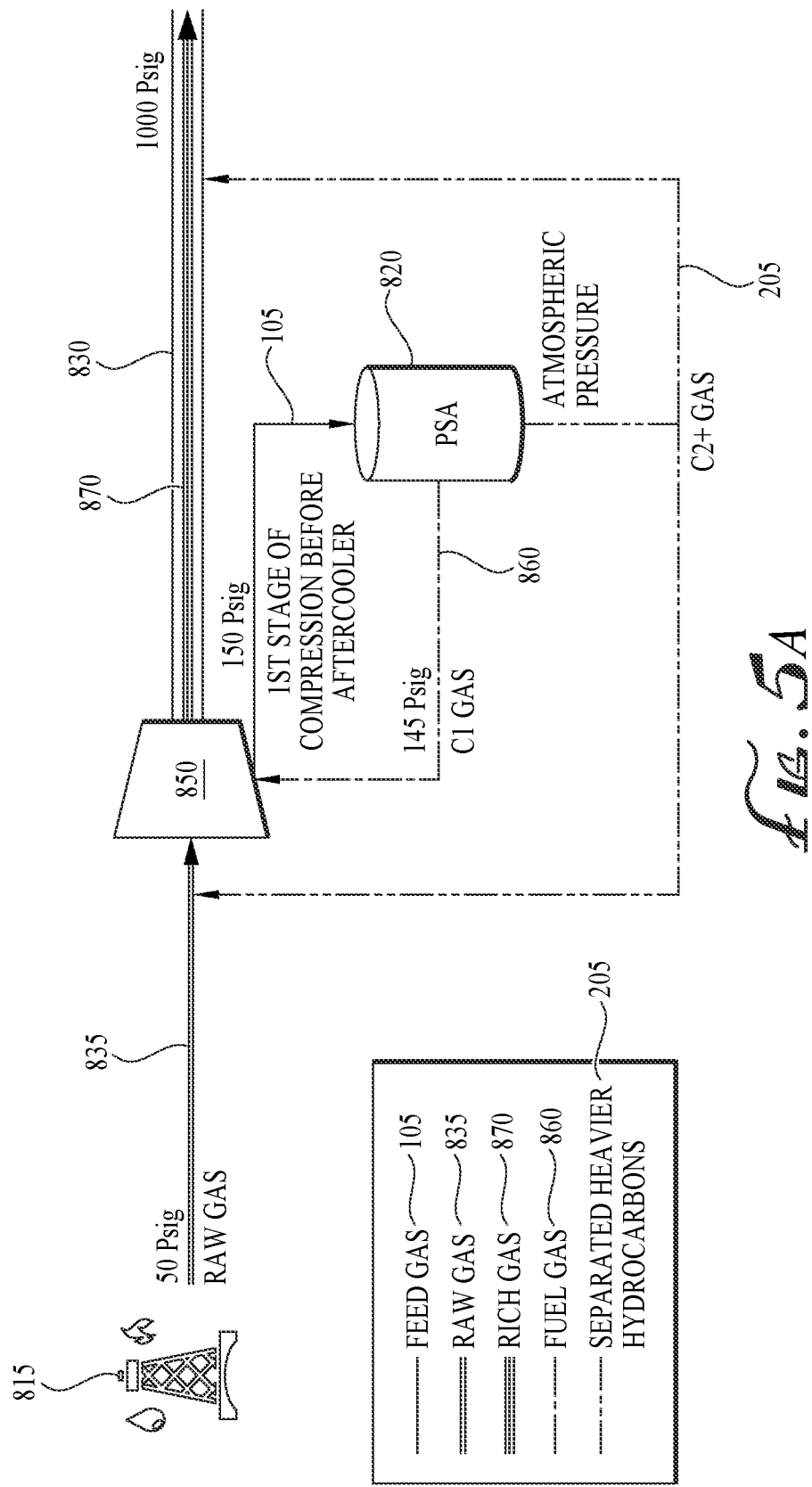

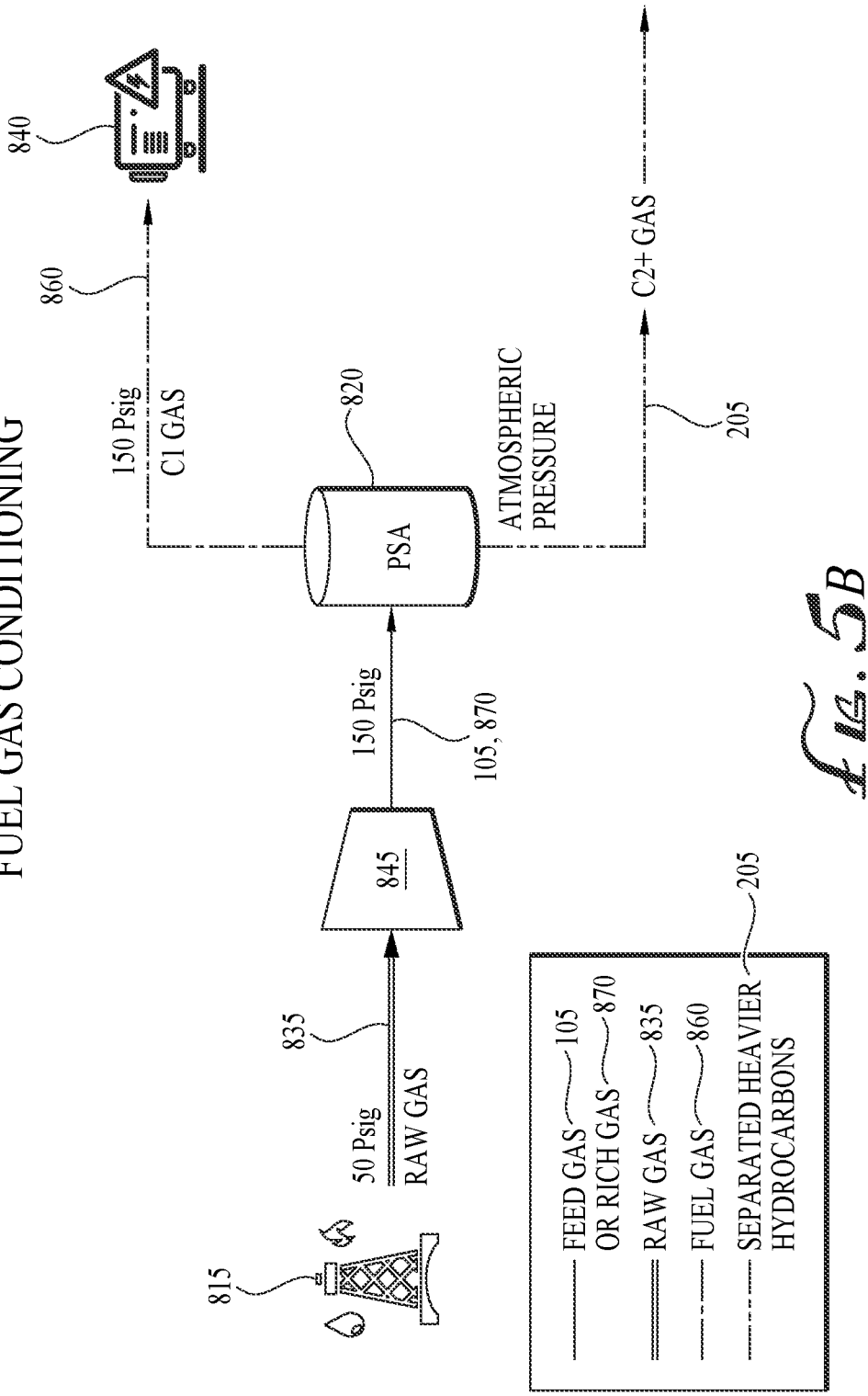

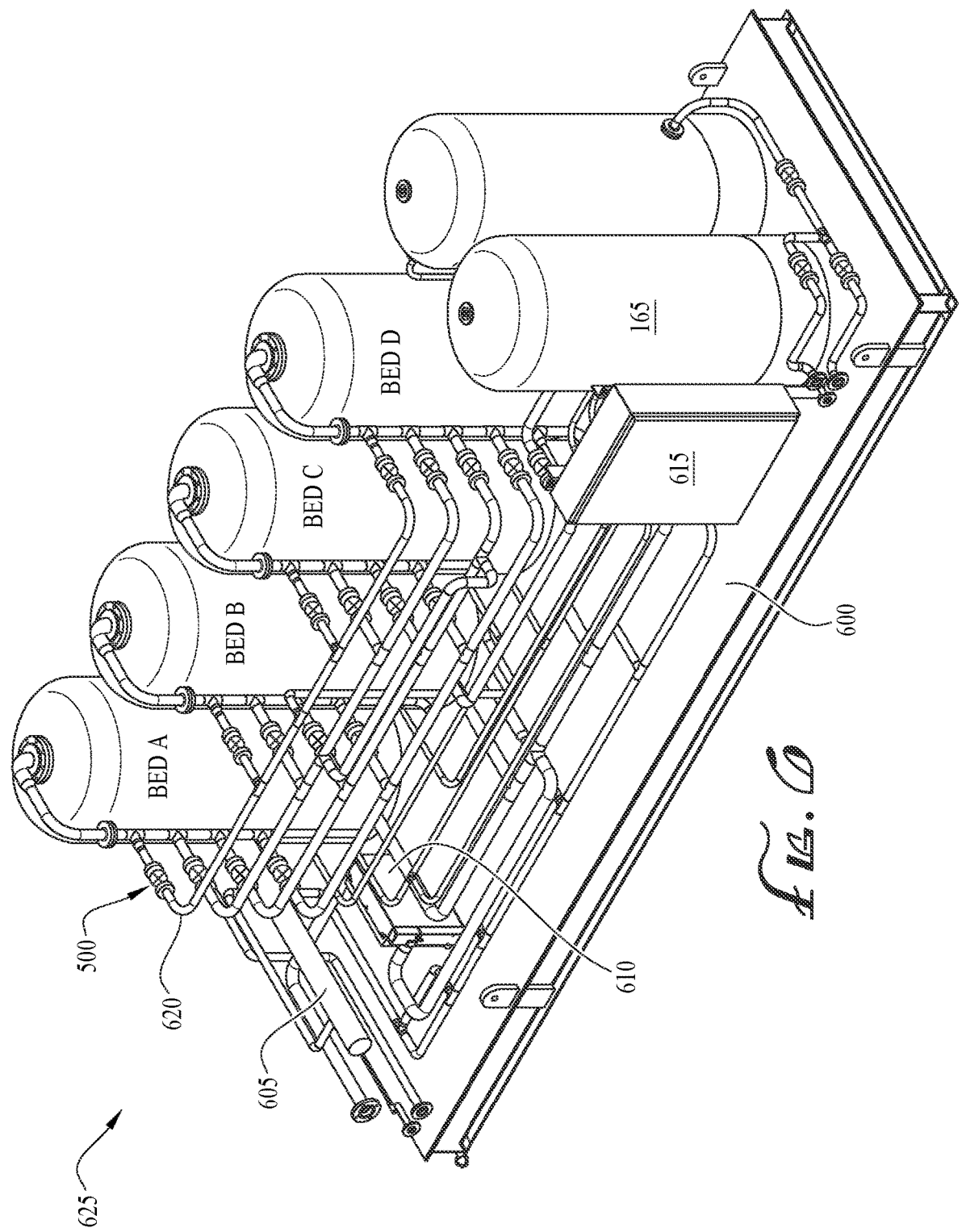

PORTABLE PRESSURE SWING ADSORPTION METHOD AND SYSTEM FOR FUEL GAS CONDITIONING

CROSS REFERENCE TO RELATED APPLICATIONS

This application claims the benefit of U.S. Provisional Application No. 63/323,628 to Ho et al., filed Mar. 25, 2022 and entitled "PORTABLE PRESSURE SWING ADSORPTION METHOD AND SYSTEM FOR FUEL GAS CONDITIONING," and also claims the benefit of U.S. Provisional Application No. 63/242,396 to Ho et al., filed Sep. 9, 2021 and entitled PORTABLE PRESSURE SWING ADSORPTION METHOD AND SYSTEM FOR LOW FLOW RATE GAS PROCESSING AND FUEL GAS CONDITIONING, each of which is hereby incorporated by reference for all purposes, except to the extent that the incorporated material is inconsistent with the express disclosure herein, in which case the language in this disclosure controls.

BACKGROUND OF THE INVENTION

1. Field of the Invention

Embodiments of the invention described herein pertain to the field of conditioning associated hydrocarbon gas from oil wells and gas wells rich in liquids. More particularly, but not by way of limitation, one or more embodiments of the invention enable a portable pressure swing adsorption method and system for fuel gas conditioning.

2. Description of the Related Art

Natural gas is often found in association with oil at production sites such as wellheads. The associated natural gas is typically a combination of methane, ethane, propane, butane, isobutane, pentane, natural gasoline, and other impurities. Production sites often include equipment that combust natural gas as fuel and/or require electricity to operate. For example, electric power generators or natural gas fuel may be required to power wellsite equipment, compressors stations, pumps and other fluid moving equipment to lift the gas and/or to gather the gas from the various wellsites and move it to a larger, centralized processing facility, which is typically a fractionation facility.

As a result, most production sites combust associated gas "as-is" as fuel to provide the energy or motive force required to collect and move produced fluids through a pipeline or gathering system. Unfortunately, this raw, unprocessed gas, is rich in heavier hydrocarbons and does not meet industry or engine manufacturer requirements as good quality fuel. Some combustion engine manufacturers use Methane Number or Wobbe Index as a proxy or indicator for a gas composition's fuel quality for a particular engine. Numerous problems related to equipment operations and maintenance are associated with using poor-quality fuel, such as pre-detonation (knock) issues, combustion chamber deterioration, increased valve recessions, de-rates and lower energy efficiency, and much higher emissions, especially with regards to volatile organic compounds, which will greatly impact air quality. Also, use of poor-quality fuel results in lower mechanical reliability and engine inefficiencies leading to increased production losses and a significant reduction in the useful lifetime of the engine. Therefore, continuing the conventional approach of combusting rich gas and emitting higher volatile organic compounds (VOCs) into the atmosphere is not a desirable, efficient or sustainable option long-term. Cleaner, better gas is needed for better engine performance.

Attempts have been made to use high-pressure fuel conditioning technologies with consumables and heavy gas recycling, such as Joule-Thomson (JT) units or membrane separation. However, a JT unit can require anywhere from 250 psi to 800 psi differential pressure to operate, while only achieving a low percentage recovery of natural gas liquids (NGLs), and often times require methanol injection or other freeze protection additives into the stream, thereby introducing further contaminants and costs into the separated energy products. Membranes have similar problems, typically requiring a minimum of 300 psia to push the fluids through the membrane.

Adsorption is a technology that has been used with limited success for the separation of hydrocarbons. Traditionally, adsorption has been used to capture liquid hydrocarbons entrained in the gas stream or for removal of water vapor in gas streams, such as mol sieve dehydration, which is conventionally recognized as a type of thermal-swing adsorption process. For gas processing purposes, the lower limit of methane in the feed gas composition is typically 80.0 mol %, and the gross heating value must be lower than 1,200 British thermal units (Btu) per standard cubic foot (scf). This significantly limits the commercial viability of conventional pressure swing adsorption separation methods because many wells produce associated gas that does not meet either gas composition limitations or the gross heating value criteria, and any pretreatment or blending of the input gas prohibitively increases the cost and footprint—quickly making the procedure cost-inefficient, particularly for fuel gas conditioning purposes.

Therefore, there is a need for an improved pressure swing adsorption method and portable system for fuel gas conditioning at low operating pressure to ensure high-quality gas with a high Methane Number is used as fuel at wellsites, compressor stations and gathering systems, and in situations where rich gas is being consumed as fuel for power generation purposes, such as for oil and gas drilling and well fracturing using electric motor frac pumps (e-fracking) applications or remote power demands.

As is apparent from the above, there is a need for a portable pressure swing adsorption method and system for fuel gas conditioning.

BRIEF SUMMARY OF THE INVENTION

One or more embodiments of the invention enable a compact, improved pressure swing adsorption method and system for fuel gas conditioning, which may be portable.

A portable pressure swing adsorption method and system for fuel gas conditioning is described. An illustrative embodiment of a fuel gas conditioning system includes a pressure swing adsorption (PSA) system configured to be fluidly coupled to at least a portion of a rich gas stream, the PSA system including a plurality of adsorbent beds and configured to condition the at least portion of rich natural gas and produce a high-quality fuel gas and gaseous separated heavier hydrocarbons when so fluidly coupled, a product end of the plurality of adsorbent beds configured to be fluidly coupled to a fuel gas line, wherein the high-quality fuel gas is discharged from the product end and supplied to the fuel gas line when so fluidly coupled, and a feed end of the plurality of adsorbent beds configured to be fluidly coupled to the at least the portion of the rich gas stream, wherein the gaseous separated heavier hydrocarbons so produced are recirculated into the one of the rich natural gas stream or a raw natural gas stream.

In some embodiments, the fuel gas conditioning system further includes a gas gathering system, wherein the gas gathering system includes the rich natural gas. In certain embodiments, the gas gathering system includes a compressor, and wherein the rich gas stream exits a first stage of discharge of the compressor. In some embodiments, the compressor is coupled between the raw natural gas stream and the rich natural gas stream. In certain embodiments, the PSA system further includes one of a heater or a heat exchanger, and the feed end of each of the plurality of adsorbent beds accepts the at least the portion of rich natural gas at a temperature of at least 100° C. In some embodiments, PSA system is configured to condition the at least a portion of the rich natural gas adiabatically at the temperature of at least 100° C. In certain embodiments, the PSA system operates in an adsorption and desorption cycle, and each one of the plurality of adsorbent beds accepts the at least a portion of the rich natural gas in sequence during the adsorption and desorption cycle. In some embodiments, a first adsorbent bed of the plurality of adsorbent beds produces the high-quality fuel gas during a same time increment as a second adsorbent bed of the plurality of adsorbent beds produces the gaseous separated hydrocarbons. In certain embodiments, upon conclusion of the time increment, the first adsorbent bed transfers pressurized gas to the second adsorbent bed. In some embodiments, the PSA system further includes a buffer tank, the buffer tank fluidly coupling purge gas between two beds of the plurality of adsorbent beds. In certain embodiments, a portion of the fuel gas is diverted to an adsorbent bed of the plurality of adsorbent beds undergoing a fuel gas pressurization (FGP) step, the diverted portion of the fuel gas configured to re-pressurize the adsorbent bed undergoing the FGP step. In some embodiments, the PSA system is self-contained on one or more portable skids. In certain embodiments, the rich gas stream is exiting a first stage of discharge of a compressor.

Illustrative embodiments of a fuel gas conditioning method includes connecting a fuel gas conditioning system to a rich gas stream discharged from one of a first stage of compression, a single-stage compressor, at 50-215 psia, or a combination thereof, wherein the fuel gas conditioning system includes a pressure swing adsorption (PSA) system, heating at least a portion of the rich gas stream to at least 100° C., accepting the heated at least the portion of the rich gas stream as feed gas into the fuel gas conditioning system, flowing the feed gas through the PSA system, wherein the PSA system adsorbs at least a portion of ethane-plus (C2+) hydrocarbons from the feed gas to produce a high-quality fuel gas, fluidly coupling the high-quality fuel gas to a fuel line, adiabatically at at least 100° C. lowering the pressure of the adsorbent bed to desorb the at least the portion of C2+ hydrocarbons, wherein the portion of C2+ hydrocarbons so desorbed are in gaseous form, and returning the gaseous at least the portion of C2+ hydrocarbons to one of the rich gas stream, a raw gas stream or a gas gathering system.

In some embodiments, the rich gas stream is discharged at 50-215 psia. In certain embodiments, the PSA system includes a plurality of adsorbent beds, and wherein a first adsorbent bed of the plurality of adsorbent beds produces the high-quality fuel gas during a same time increment as a second adsorbent bed of the plurality of adsorbent beds produces the desorbed C2+ hydrocarbons. In some embodiments, a product end of the first adsorbent bed discharges the high-quality fuel gas and a feed end of the second adsorbent bed returns the gaseous C2+ hydrocarbons to the one of the rich gas stream, the raw gas stream or the gas gathering system. In certain embodiments, upon conclusion of the time increment, the first adsorbent bed transfers pressurized gas to the second adsorbent bed. In some embodiments, the PSA system further includes a buffer tank, the buffer tank fluidly coupling a purge gas between a third bed of the plurality of adsorbent beds and the second adsorbent bed. In certain embodiments, a portion of the fuel gas is diverted to an adsorbent bed of the plurality of adsorbent beds undergoing a fuel gas pressurization (FGP) step, the diverted fuel gas re-pressurizing the adsorbent bed undergoing the FGP step. In some embodiments, the high-quality fuel gas flowing through the fuel line powers an engine in the gas gathering system. In certain embodiments, the fuel gas conditioning system is portable. In certain embodiments, the PSA system comprises four adsorbent beds and cycles through seven steps in an adsorption and desorption cycle.

In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

Advantages of the present invention may become apparent to those skilled in the art with the benefit of the following detailed description and upon reference to the accompanying drawings in which:

FIG. 1 is a schematic diagram of a fuel gas conditioning adsorption process of illustrative embodiments.

FIG. 2 is a table illustrating a four-bed adsorption process of illustrative embodiments for fuel gas conditioning.

FIGS. 3A-3L are schematic diagrams of twelve time increments of a fuel gas conditioning adsorption process of illustrative embodiments.

FIG. 4 is a schematic diagram of four-bed adsorption system of illustrative embodiments for fuel gas conditioning.

FIGS. 5A-5B are schematic diagrams of fuel conditioning systems of illustrative embodiments.

FIG. 6 is a perspective view of a portable fuel gas conditioning system of illustrative embodiments.

Figure 3A:
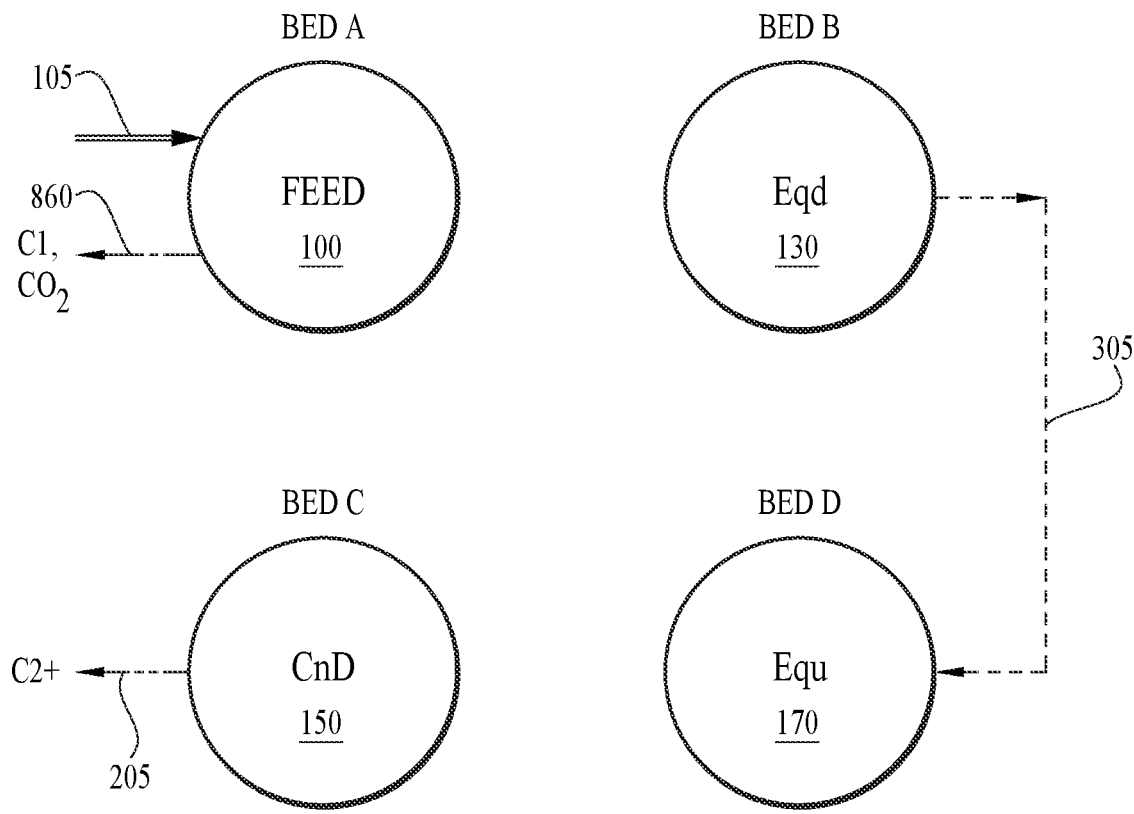

While the invention is susceptible to various modifications and alternative forms, specific embodiments thereof are shown by way of example in the drawings and may herein be described in detail. The drawings may not be to scale. It should be understood, however, that the embodiments described herein and shown in the drawings are not intended to limit the invention to the particular form disclosed, but on the contrary, the intention is to cover all modifications, equivalents and alternatives falling within the scope of the present invention as defined by the appended claims.

DETAILED DESCRIPTION

A portable pressure swing adsorption method and system for fuel gas conditioning will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

As used in this specification and the appended claims, the singular forms "a", "an" and "the" include plural referents unless the context clearly dictates otherwise. Thus, for example, reference to an adsorption bed includes one or more adsorption beds.

As used herein "vacuum" means a pressure lower than atmospheric pressure, which is about 14.7 psia.

As used in this specification and the appended claims, "low flow rate" means 5,000,000 standard cubic feet per day or less, where "standard" refers to a temperature of 15.56° C. (60° F.) and a pressure of 14.7 psia (atmospheric pressure).

As used in this specification and the appended claims, when in reference to natural gas fuel, "high-quality" means a gross heating value of less than or equal to 1,100 Btu/scf. In this specification, "lean fuel" and "high-quality fuel" are used interchangeably to refer to natural gas having a gross heating value of less than or equal to 1,100 Btu/scf.

As used in this specification and the appended claims, "separated heavier hydrocarbons" means gaseous alkane hydrocarbon compounds with molecular weights greater than methane and having the exemplary compositions as specified in Tables 3-4. Those of ordinary skill in the art of hydrocarbon treatment and processing would understand the scope of "separated heavier hydrocarbons" in view of this definition and the examples provided herein. When compressed, cooled, and/or fractionated, separated heavier hydrocarbons may form natural gas liquids (NGL). In illustrative fuel gas conditioning embodiments described herein, the recovery percentage of methane in the conditioned fuel gas may be less than 90%, and therefore unrecovered methane may also be mixed with the separated heavier hydrocarbons of illustrative embodiments.

As used in this specification and the appended claims, "light reflux" is an intermediate step in the process of illustrative embodiments for fuel gas conditioning, which circulates depressurized, intermediate gas (purge gas) that on average is heavier than fuel gas but lighter than the separated heavier hydrocarbons, in a manner more specifically described herein.

"Rich" in reference to natural gas, means gas having an energy content per standard cubic foot that exceeds 1,100 Btu/scf. "Raw gas" means untreated, unprocessed and unconditioned gas in such form as it is produced from a wellsite or other natural or artificial formation. Raw gas may be rich gas if the raw gas meets the energy content criteria described herein, and raw gas that is treated and/or compressed in some manner prior to conditioning may form rich gas if the gross heating value of such gas is greater than 1,100 Btu/scf.

As used herein, a "remote location" refers to a location that does not have access to existing infrastructure allowing for commodity market access, in most instances such commodity market access requires pipeline infrastructure to the trading hubs or major consumption centers, such as, for example, Henry Hub, Waha, or Chicago Citygate.

In the art, "Methane Number" is a measure of the resistance of natural gas to detonation when the natural gas is combusted as fuel in an engine. Pure methane is assigned a Methane Number of 100 and pure Hydrogen is assigned a Methane Number of zero. There is no universally accepted method for calculating Methane Number based on composition. Each engine manufacturer, such as INNIO Waukesha Gas Engines of Innsbruck, Austria, Caterpillar Inc. of Texas, United States, Wartsila Corporation of Helsinki, Finland and Cummins Inc. of Indiana, United States, has their own calculation and "Methane Number." As used herein, in reference to fuel gas, a "sufficiently high Methane Number" or "high Methane Number" means that the fuel gas will meet the Methane Number requirement of any recognized engine manufacturer of natural-gas fueled engines as of the date of this filing.

In the art of hydrocarbon treatment, alkane hydrocarbon compounds having two carbon atoms in a chain per molecule are typically referred to as C2, hydrocarbon compounds having three carbon atoms in a chain in a molecule are referred to as C3, etc. For example, methane may be referenced as C1, ethane as C2, propane as C3, and so on. The annotation C2+ refers to alkane hydrocarbon compounds having two or more carbon atoms in a chain per molecule of the hydrocarbon, such as ethane, propane, butane and heavier hydrocarbons. In addition, C2 is considered "heavier" than C1, C3 "heavier" than C2, etc.

While for ease of description and so as not to obscure the invention, illustrative embodiments herein are described in terms of wellsite fuel gas conditioning of associated raw gas or rich gas. However, illustrative embodiments are not so limited and may be equally applicable to situations outside of a wellsite. For example, illustrative embodiments may be employed for fuel gas conditioning purposes at a larger gathering system, tank battery and/or compressor station. In such instances, the gathered gas may be rich gas and illustrative embodiments may be employed as a small, portable system to process a slipstream of such rich gas to fuel a natural gas engine-driven compressor, such that the engine may operate more efficiently. In another example, illustrative embodiments may reduce the Btu of the fuel feeding a gas engine in an oil and gas producing area or field. Illustrative embodiments may therefore alleviate the problems rich gas may present for many engines and engine driven compressors such as the greater downtime in operations and maintenance, as well as higher emissions profile during operation when richer Btu gas is used for fuel.

Illustrative embodiments may provide a portable and compact fuel gas conditioning system that may be mobilized in and out of the field and therefore may be economical to condition stranded gas assets or infrastructure constrained locations. Illustrative embodiments may improve the Methane Number of fuel gas, which may be used to provide last mile electricity or other more environmentally productive products than the conventional combusting of rich gas or flaring of stranded assets. Illustrative embodiments may provide a single design that has a low capital cost because complex infrastructure is not required, and it is compact and robust enough to meet a wide range of low inlet pressures, such as pressures less than 100 psia, pressures less than 150 psia, and/or pressures as low as 50 psia, and a wide range of gas compositions, while providing high-quality fuel gas.

Illustrative embodiments may provide a high-temperature adsorption solution that removes heavier hydrocarbons as vapor from natural gas at 100° C. or above. Surprisingly, such high-temperature gaseous-phase approach, when applied to a pressure-swing adsorption system of illustrative embodiments, provides fuel gas conditioning efficiency in a compact, portable unit that is cost-effective and may improve the lifetime of engines and onsite gas-gathering equipment.

Much, if not all, of the separated heavier hydrocarbons (in both adsorbed and gas phases) may be recovered during a countercurrent depressurization step and countercurrent purge step, the latter of which is referred to herein as a "light reflux step," again resulting in separated heavier hydrocarbons that are more enriched in the heavy component. This purge gas may be produced from an intermediately pressurized co-current depressurization (CoD) gas (in some embodiments, after it transits from the buffer tank) into the adsorbent bed that has previously experienced pressure equalization steps at a pressure less than feed pressure. Increasing or optimizing the volume of reflux gas for this "rinsing" of the adsorbent bed may enhance the recovery of high-quality fuel gas. This light reflux step in combination with the adsorption process described herein permits illustrative embodiments to be flexible or accommodating to changes and variability in gas compositions to be conditioned by the adsorption system of illustrative embodiments.

In some embodiments, the buffer tank may be omitted and purge gas may travel directly from a bed undergoing CoD into a bed undergoing light reflux. Illustrative embodiments may advantageously avoid bed fluidization or undesirable pressure drops that plague conventional adsorption systems that unsuccessfully attempt higher throughput. Illustrative embodiments may remove the buffer tank, directly linking the cocurrent depressurization of one adsorbent bed with the light reflux step of another adsorbent bed, and may employ a structured adsorbent to successfully accomplish faster cycle times. Faster cycle times of illustrative embodiments may provide for a higher throughput in a smaller volume, without materially impacting the performance of the pressure swing adsorption (PSA) process of illustrative embodiments to produce high quality fuel gas.

Illustrative embodiments may handle a wider range of inlet gas compositions than conventional PSA cycles, while still recovering high-quality fuel gas. For example, illustrative embodiments may accommodate 1,150 Btu/scf to 1,700 Btu/scf rich gas inlet. This may be especially relevant for wellsite or remote applications, where the gas compositions and flow rates are variable and the lack of infrastructure in place prevents the blending of gas streams or gas compositions.

Illustrative embodiments provide a high temperature near-isothermal process primarily at 100° C. to 150° C., at 100° C., at at least 100° C. or at about 100° C., which brings and/or maintains all hydrocarbons present in the raw gas and/or rich gas in a gaseous phase. Conducting the fuel gas conditioning process of illustrative embodiments in a gaseous phase at an elevated temperature minimizes the adsorption of methane, may aid in the desorption of heavier hydrocarbons, and may simplify the steps that would otherwise be required in a lower-temperature PSA process. This higher temperature may also improve the regeneration of the adsorbent, thereby maintaining maximum working capacity of the adsorbent beds. An inlet heater may be employed, or a heat exchanger may reuse some of the heat generated through compression to heat the feed gas prior to it entering the inlet of the adsorption beds. Feed gas may be passed through a single stage of compression prior to entering the adsorption bed inlet to bring the feed gas to a pressure of about 100 psia, 150 psia or 50 psia to 215 psia. This single stage of compression may be inherent in the field as part of the gas gathering systems. In some embodiments, the pressure swing adsorption process of illustrative embodiments may employ gas at wellhead pressure, and no field compression may be necessary. Certain illustrative embodiments may be employed to condition gas at a booster compressor station that may be receiving gas at >150 psia, and thus the PSA system of illustrative embodiments may operate at inlet conditions. In some embodiments, the gas gathering system of illustrative embodiments may be coupled to one of a compressor station, tank battery or wellsite.

Adsorbent beds may be configured as columns (beds) of and/or containing adsorbent. An adsorbent of illustrative embodiments may be layers of highly-porous activated carbons. Silica, zeolites, molecular sieves, metal organic frameworks and/or alumina may also be employed as adsorbents. Exemplary adsorbents are offered by Cabot Corporation (Georgia, USA), Calgon Carbon Corporation (Pennsylvania, USA), Puragen Activated Carbons (Palm Beach Gardens, Fla., USA), and Ingevity Corporation (South Carolina, USA). Adsorbents may be packed inside columns (beds) with loading access at both ends to form the adsorbent bed. An orifice and pressure regulator may provide precise gas flow through the bed. The adsorbents used in these illustrative embodiments may also be structured or monolithic in nature, in addition to the more traditionally shaped form factors of beads, pellets, or granules. A back-pressure regulator may place the system under a preset pressure. Optionally, the connection of a vacuum pump or fluid differential pressure pump may enhance the regeneration ability for the adsorbents. However, in illustrative embodiments, no rotating equipment or vacuum pump, outside of compression inherent in the field, may be necessary.

Fuel Gas Conditioning

Illustrative embodiments may be employed to accomplish fuel gas conditioning to operate engines for power generation and/or for field equipment such as compressors that are inherent in the field for moving produced fluids through gathering and/or transport pipelines. In the fuel gas conditioning method of illustrative embodiments, a high-quality fuel gas for consumption (for example as fuel to provide the energy or motive force required to collect and move produced fluids through a pipeline or gathering system) may be produced. More specifically, the high-quality fuel gas may have less than 1,100 Btu/scf gross heating value. Recovery percentage of methane may not be of concern in fuel gas conditioning embodiments, because separated heavier hydrocarbons from the fuel gas conditioning process of illustrative embodiments may be recycled for further collection and/or processing and therefore such separated heavier hydrocarbons may be mixed with any unseparated methane.

The reader may first consider FIG. 6, which illustrates a portable fuel conditioning system of illustrative embodiments. Portable fuel gas conditioning system 625 may be arranged on portable skid 600, which may be less than eight feet wide and meet U.S. Department of Transportation requirements for road transport. Adsorbent beds, such as Bed A, Bed B, Bed C and Bed D may be arranged on skid 600. Adsorbent beds may be fluidly connected and/or coupled by piping 620 and a valve and/or a system of switching valves 500. Heater 605, which may be heat exchanger 505 (shown in FIG. 4), may increase the temperature of feed gas 105 to at least 100° C. and/or to a temperature that brings and/or maintains all hydrocarbons present in the raw gas or rich gas in a gaseous phase. Control panel 615 may control valve 500 and/or fluid flow, and may be pre-programmed or manually controlled. When included, buffer tank 165 may also be secured to skid 600. In some embodiments, buffer tank 165 may not be necessary and may be omitted from the skid and portable fuel gas conditioning system 625.

Turning to FIGS. 5A and 5B, illustrative embodiments may employ PSA system 820 and/or fuel gas conditioning system 625 to receive feed gas 105 directly from wellhead 815 or after only a single stage of compression, to condition feed gas 105 and produce fuel gas 860 and separated heavier hydrocarbons 205. In some embodiments, PSA system 820 may be and/or may be packaged as portable fuel gas conditioning system 625 (shown in FIG. 6).

In FIG. 5A, raw gas 835 may be produced from wellhead 815, the field, and/or a hydrocarbon formation. Raw gas 835 may be removed from wellhead 815 at a wellhead pressure of about 50 psia and be transported to multi-stage compressor 850 for gas gathering. A slipstream of feed gas 105, which may be a portion of rich gas 870 being discharged from multi-stage compressor 850 for gas gathering, may be taken from the output of the first stage of compression from multi-stage compressor 850. Feed gas 105 may, for example, be at 100 psia, or at 150 psia having passed through one stage of compression, or anywhere from 50-215 psia. In some embodiments, multi-stage compressor 850 may be single-stage compressor 845 (shown in FIG. 5B). The remainder of rich gas 870 may continue through additional stages of compression in multi-stage compressor 850 and be sent through rich gas discharge line 830 at, for example, about 1,000 psig.

Slipstream of feed gas 105 may be processed in PSA system 820 of illustrative embodiments, and the lean gas produced, such as fuel gas 860, may be high-quality gas and/or have a sufficiently high Methane Number to function as good quality fuel for an engine or other fuel-consuming equipment. For example, fuel gas 860 may be returned at pressure to multi-stage compressor 850 to be used as fuel for multi-stage compressor 850. Separated heavier hydrocarbons 205, which may be the remaining gas after separation of fuel gas 860 from rich gas 870, and which may be mixed with unseparated methane, may be returned to rich gas discharge line 830 for further downstream processing (such as for example, processing at a fractionation facility), and may be returned to the inlet of suction of multi-stage compressor 850 at 50 psia or at any pressure slightly greater than the pressure of raw gas 835.

Turning to FIG. 5B, raw gas 835 may be taken from wellhead 815 or the field and treated and/or compressed in single-stage compressor 845. Discharge from single-stage compressor 845 may be processed in PSA system 820 to produce lean, high-quality fuel gas 860 for power generation such as for micro-grid 840 or onsite power usage. Separated heavier hydrocarbons 205 may be sent for further downstream processing. Fuel gas conditioning may be possible using PSA system 820 for any stream of rich gas 870 pressurized between 50 psia to 215 psia. In the embodiment of FIG. 5B, feed gas 105 may be pressurized gas from single-stage compressor 845. In addition, if wellhead 815 has pressure from 50 psia to 215 psia, then compression, such as for example compression from single-stage compressor 845, may not be necessary and raw gas 835 may serve as feed gas 105.

The PSA System

Illustrative embodiments may include an adsorption and desorption cycle having four adsorbent beds, and with each bed cycling through seven steps. In fuel gas conditioning embodiments, the desired product may be a high-quality fuel gas 860, with a high Methane Number. Each bed may interact with one another to provide an efficient cycle to produce high-quality fuel gas 860. Each of the beds may be conditioning gas at any given time increment, with each bed at a different step in the cycle of illustrative embodiments at such time increment. As such, if one bed is on a step that moves gas to another step, the gas may move from one bed to another.

Now turning to FIG. 1, the reader will note that FIG. 1 illustrates a schematic diagram overview of a portable fuel gas conditioning method of illustrative embodiments. FIG. 2 is a table providing the relative process step of each bed, at each time increment, as the method cycles through the beds in the method of FIG. 1, with each bed at a different phase of the cycle at differing times. Table 1 provides an illustrative example of operating conditions including the timing of the steps shown in FIG. 2. The operating conditions represented in Table 1 are exemplary only and not intended to be limiting.

TABLE 1

Exemplary Operating Conditions of Fuel Gas Conditioning Illustrative Embodiments

| Operating Conditions | |
| --- | --- |
| X, s | 40 or 160 |
| Feed time, s | 200 + x |
| CoD and FGP time, s | 120 + x |
| CoD Pressure, Psia(kPa) | 50.7 (350) |
| Cycle Time (CT), s | 960 or 1440 |
| Feed Pressure, Psia | 50-215 psia |
| Feed Temperature | at least 100° C. |

In embodiments where buffer tank 165 is omitted, the x of Table 1 may be zero.

The method of FIG. 1 of illustrative embodiments may be operated using the exemplary system of FIG. 4. As shown in FIG. 4, Bed A, Bed B, Bed C and Bed D may be fluidly coupled together using piping and valve system 500 to control fluid flow. Heat exchanger 505 and/or heater 605 may raise the temperature of feed gas 105 entering a bed undergoing feed step 100. For the fuel gas conditioning example of FIG. 4, no pumps, compressors or other rotating equipment may be necessary for the method of FIG. 1, other than compression inherent in the field from a compressor such as multi-stage compressor 850 or single-stage compressor 845.

As is apparent from FIG. 6, no rotating equipment is included in the portable fuel gas conditioning system of illustrative embodiments. PSA system 820 of illustrative embodiments, may be employed after a first stage of compression (single-stage compressor 845 or multi-stage compressor 850) in the field, before aftercooler 610, which aftercooler 610 may be included on skid 600, to accomplish fuel conditioning, which may result in high-purity fuel gas 860 and may be used to power single-stage compressor 845, multi-stage compressor 850, or provide fuel for power generation for micro-grid 840 or other onsite use. Higher feed pressure, such as feed pressure at 100 psia or 150 psia after a single-stage of field compression of rich gas 870 may reduce vessel volumes, although feed pressure may be in the range of 50-215 psia. For example, raw gas 835 at wellhead 815 pressure of 50 psia may be feed gas 105 for PSA system 820. The temperature of feed gas 105 may be at least 100° C., or may be about 150° C., which may ensure feed gas 105 has and/or maintains all component hydrocarbons in a gaseous phase during the substantially adiabatic process of illustrative embodiments (excepting only when the hydrocarbons are adsorbed during the processing of illustrative embodiments). Taking a slipstream of feed gas 105 prior to aftercoolers 610 may ensure that the gas entering PSA system 820 is hot and minimizes the system's inlet heater 605 duty. In some embodiments, fuel gas 860 may exit a bed during feed step 100 at 150 psia. Separated heavier hydrocarbons 205 may exit a bed undergoing light reflux step 160 at 14.7 psia and/or atmospheric pressure.

In some embodiments, a vacuum may be employed. In such instances, a vacuum pump may bring a bed to vacuum and collect separated heavier hydrocarbons from a bed undergoing countercurrent depressurization step (CnD step) 150 (shown in FIG. 1). This vacuum pump may decrease pressure of tanks to desorb and recover separated heavier hydrocarbons under vacuum in embodiments where vacuum is employed. In some embodiments, no vacuum is necessary and sufficient pressure swing may occur without the need of a pump or any other rotating equipment.

Pressure Swing Adsorption (PSA) Method Steps

With reference to FIG. 1, this description follows FIG. 2 across row 200 and is therefore from the perspective of Bed A for ease of description and so as not to obscure illustrative embodiments. Those of skill in the art will understand that the description could similarly follow the perspective of Bed B, Bed C or Bed D. At feed step 100, feed gas 105 may first be pressurized to between about 50 psia-215 psia as more specifically described herein. If the pressure of fluid exiting wellhead 815 and/or the downhole formation is at least 50 psia, then no compression may be necessary. If greater pressure is desirable, a single stage of compression, for example compression from single-stage compressor 845 inherent in the field, or from the first stage of multi-stage compressor 850 inherent in the field, may be applied to feed gas 105 to raise the pressure of feed gas 105 to 100 psia, about 100 psia, 150 psia or about 150 psia. Some inlet feed pressure is desirable for the pressure-swing adsorption method to optimize or minimize its equipment footprint, because pressure is inversely proportional to volume. In some embodiments, multiple-stages of compression and/or one or more pumps, such as a centrifugal pump or fluid differential pressure pump, may be employed to bring feed gas 105 up to a pressure of 50 psia to 215 psia, or above. However, those of skill in the art will appreciate that a pump and/or multiple stages of compression may not be required to arrive at the desired pressure range of 50 psia to 215 psia, and the absence of such rotating equipment may desirably conserve energy and cost. In illustrative embodiments, only a single stage of compression may be necessary to permit fuel gas conditioning. Conventional pressure swing adsorption systems typically require pressures around 500 psia, which requires more energy for pressurization than illustrative embodiments described herein. Specific output pressure of feed gas 105 may depend upon wellhead 815 pressure and the number of stages of compression. In the example of FIG. 1 and Table 1, feed gas 105 may be brought to 100 psia or to 150 psia.

Feed gas 105 may be heated to at least 100° C., or to 100-150° C. Heating feed gas 105 to at least 100° C. may ensure that all constituents of feed gas 105 remain in a gaseous phase during the adsorption cycle of illustrative embodiments. Contrary to conventional expectations, removing water, impurities and the separated heavier hydrocarbons from fuel gas 860 is more efficient, improved and requires less energy investment in compression and/or pressurization when carried out in a gaseous phase, rather than conventional methods that allow liquids to "drop out" at lower temperatures. Adsorption of unwanted adsorbates, such as methane for fuel gas conditioning purposes, may be minimized and regeneration of the adsorbent beds may be improved at temperatures of at least 100° C. A heater 605 may be employed to heat feed gas 105 and/or heat exchanger 505, such as a double tube heat exchanger, shell-and-tube heat exchanger, tube in tube heat exchanger, or plate heat exchanger, may be employed to recirculate some of the heat generated through compression to heat the gas prior to inlet into Bed A. Heating feed gas 105 to 100-150° C. or to at least 100° C., may minimize adsorption of methane into the adsorbent and may help regenerate the adsorbent bed by providing more energy for desorption. The cycle of illustrative embodiments may be isothermal and/or substantially adiabatic such that the conditioned fluids remain in a gaseous phase throughout the process of illustrative embodiments.

Feed gas 105 may be a mixture of various continuous-chain alkane hydrocarbons, such as methane, ethane, propane, butane, pentane and/or octane and/or may be associated gas from a production well, such as an oil well or gas well rich in natural gas. Contaminants such as nitrogen, carbon dioxide, water and/or hydrogen sulfide may also be present in feed gas 105 and/or may be removed prior to entry into Bed A. Bed A may include layers of activated carbon, silica, zeolites, molecular sieves, metal organic frameworks, alumina, or another similar adsorbent that may adsorb C2+ or C3+ hydrocarbons and produce a non-adsorbed methane as fuel gas 860. More than one type of adsorbent may be employed in the bed as separate layers to either enhance adsorption of heavier hydrocarbons or to aid in the adsorption of other contaminants, such as water, hydrogen sulfide or carbon dioxide.

In FIG. 1 at feed step 100, feed gas 105 may flow through Bed A entering at feed end 125 of the bed and exiting at product end 135 of the bed. The throughput during feed step 105 may for example be pumped through Bed A at 4,000 standard liters per minute or approximately 200,000 standard cubic feet per day (scfd). In another embodiment, the throughput may be increased to, for example, 500,000 scfd or 10,000 standard liters per minute by decreasing the cycle time. In this manner, more gas may be conditioned in the same adsorbent volume. As long as the adsorption and desorption kinetics of heavier adsorbates allow, cycle times for this method may be decreased even further to permit even higher throughput than 500,000 scfd. Hydrocarbons in feed gas 105 that are heavier than methane, such as ethane, propane and/or butane, may be adsorbed by the adsorbent, whilst the methane may pass through Bed A without adsorbing and may be collected as fuel gas 860. Other impurities such as nitrogen and carbon dioxide may also pass through Bed A during feed step 100.

A portion 115 of gaseous fuel gas 860 may be diverted to fuel gas pressurization (FGP) step 180 to increase the pressure of another bed that has already desorbed the separated heavier hydrocarbons 205 and thus been regenerated. For example, as shown in row 240 of FIG. 2, Bed D may undergo FGP step 180 at the same time Bed A undergoes feed step 100, therefore a portion 115 of fuel gas 860 exiting from Bed A, may flow in a countercurrent into Bed D for re-pressurization of Bed D, in preparation for Bed D to repeat feed step 100. Portion 115 of fuel gas 860 may be used to re-pressurize the bed at the very end of the cycle (i.e., FGP step 180) in order to set up restart of the cycle.

Equalization down step (EqD step) 130 may follow feed step 100 for Bed A and/or may begin once feed gas 105 ceases to enter Bed A. During equalization down step 130, the pressure in Bed A may be reduced from the initial feed gas pressure in order to begin desorbing hydrocarbons adsorbed by Bed A during feed step 100. Pressure may be reduced by removing pressurized gas 305 from the product end 135 of Bed A, and sending such pressurized gas 305 into the product end 135 of another bed undergoing equalization up step (EqU step) 170 in a countercurrent manner, Bed C in this example. Pressurized gas 305 will be at a pressure lower than feed gas 105, but at a higher pressure than atmospheric pressure and/or a higher pressure than purge gas 155 because the pressure reduction from feed pressure to atmospheric pressure may be incremental.

EqD step 130 may be the first depressurization and/or desorption step in the PSA cycle of illustrative embodiments. The purpose of this equalization down step 130 may be to enrich Bed A with gaseous separated heavier hydrocarbons, as may occur as the pressure begins to lower inside Bed A. In one illustrative example, pressure may be reduced inside Bed A from an initial pressure of 150 psia to 100 psia during equalization down step 130. As further described herein, depressurization may occur in multiple steps and/or stages. Some of the separated heavier hydrocarbons 205, such as ethane and propane may desorb during equalization down step 130, and such pressurized gas 305 may be circulated to a bed undergoing equalization up step 170. For example, in the embodiment of FIG. 2, when Bed A is undergoing equalization down step 130, Bed C is simultaneously undergoing equalization up step 170, so pressurized gas 305 may flow from Bed A to Bed C, thereby utilizing pressurized gas 305 to simultaneously lower the pressure within Bed A and increase the pressure within Bed C.

Cocurrent depressurization step (CoD step) 140 may be an additional depressurization step for Bed A, for example reducing the pressure inside Bed A from 100 psia or 75 psia to 50 psia. As used herein, "cocurrent" refers to the direction of gas leaving a bed during cocurrent depressurization step 140, which flows in the same direction that feed gas 105 had flowed through such bed (for example, from feed end 125 towards product end 135). As used herein, "countercurrent" means flow in the opposite direction to "cocurrent."

Pressure may be reduced inside Bed A during cocurrent depressurization step 140 by removing desorbed purge gas 155 from the bed. Purge gas 155 may be at an intermediate pressure between the pressure of feed gas 105 and atmospheric pressure and/or between the pressure of pressurized gas 305 and atmospheric pressure. Further depressurization may allow yet heavier and/or additional hydrocarbons to desorb from the adsorbent Bed A. Buffer tank 165 may be a buffer tank without adsorbent, which may provide another pressure decrease in the desorption process. During CoD step 140, desorbed purge gas 155 may be collected and/or held in buffer tank 165 and/or flowed in a countercurrent manner (from product end 135 towards feed end 125) into a bed undergoing light reflux step (LR step) 160. Use of buffer tank 165 may also allow for additional removal of lighter gases from the bed prior to recovery of separated heavier hydrocarbons 205 under vacuum and/or the lowest pressure reached during the cycle of illustrative embodiments. In some embodiments, one bed may be undergoing cocurrent depressurization step 140 at the same time another bed is undergoing light reflux step 160, and buffer tank 165 may not be necessary. Purge gas 155 from CoD step 140 may be sent directly to a bed undergoing LR step 160 and/or be sent first to buffer tank 165 and then to a bed undergoing LR step 160.

During CnD step 150, fluid exiting Bed A flows in a direction opposite the flow of feed gas 105 and/or exits Bed A at the feed end 125 of Bed A (for example, may exit Bed A on the same side of the bed that feed gas 105 enters Bed A). During CnD step 150, pressure may be reduced inside Bed A to the lowest pressure that will be experienced by Bed A during the adsorption/desorption cycle, which may be atmospheric pressure (approximately 14.7 psia). Pressure may be reduced by the countercurrent removal of separated heavier hydrocarbons 205. Pressure may be optionally reduced to a vacuum, for example from 25 psia to 2-6 psia and/or to a pressure below atmospheric pressure, through the use of a pump. In fuel gas conditioning embodiments, a vacuum may optionally be applied to improve recovery or improve working capacity of the bed, but such may not be necessary and therefore may eliminate the mechanical complexity of operating a system under constant vacuum. In certain embodiments, the gas regenerated and recovered during CnD step 150 and/or LR step 160 may constitute separated heavier hydrocarbons 205. During CnD step 150, separated heavier hydrocarbons 205 may be desorbed and/or removed from feed end 125 of Bed A. Separated heavier hydrocarbons 205 may be C2+ hydrocarbons and/or may be gaseous when desorbed from adsorbent within Bed A.

When Bed A enters LR step 160, purge gas 155 may flow from a bed undergoing CoD step 140 and/or from buffer tank 165, if optionally employed, in a countercurrent direction through Bed A. In some embodiments, purge gas 155 may flow directly from a bed undergoing CoD step 140 and buffer tank 165 may not be necessary. Omitting buffer tank 165 may permit faster cycle times, which may increase throughput while maintaining a small footprint for PSA system 820 and/or fuel gas conditioning system 625. Alternatively, inclusion of buffer tank 165 may permit independence between the timing of CoD step 140 and LR step 160. Separated heavier hydrocarbons 205 may have already been desorbed and substantially removed during CnD step 150. Purge gas 155 may originate from CoD step 140 where much of the fuel gas 860 has been previously removed. Purge gas 155 may therefore be enriched heavy gas. Even at atmospheric pressure there may be interaction between heavy gases and the adsorbent in LR step 160. Flushing Bed A with purge gas 155 may induce additional desorption of separated heavier hydrocarbons 205, which may be removed and combined with the separate heavier hydrocarbons removed during CnD step 150. This light reflux step, aided by pressurized gas (purge gas 155) flowing in a countercurrent manner, causes the strongly adsorbed components to be flushed back towards feed end 125 of the bed. This allows the majority of Bed A to be free of adsorbate and ready for the complete cycle of illustrative embodiments to be repeated. Separated heavier hydrocarbons 205 may be returned to rich gas discharge line 830 for further downstream processing, be returned to the inlet of suction of multi-stage compressor 850 at 50 psia or at any pressure slightly greater than the pressure of raw gas 835.

During equalization up step (EqU step) 170, pressure inside Bed A begins increasing with light gas to prepare Bed A to begin adsorption once again. Pressurized gas 305 from EqD step 130 of Bed C may be added into Bed A during Bed A's equalization up step 170 to increase the pressure of Bed A.

During fuel gas pressurization step (FGP step) 180, the pressure in Bed A is raised back up to 100 psia, 150 psia and/or the desired pressure to return to feed step 100, such as between 50 psia and 215 psia. A portion 115 of fuel gas 860 may be diverted to Bed A to increase the pressure. In the example of FIG. 2, Bed B is undergoing feed step 100 while Bed A is undergoing FGP step 180 and therefore in such example, portion 115 may flow from Bed B to Bed A.

Piping and valve system 500 may be employed to move and pressurized fluid between beds. Pressure may originate from wellhead 815 and/or make use of compression inherent in the field such as compression/pressurization from single-stage compressor 845 or multi-stage compressor 850. Therefore, pumps or other rotating equipment may not be necessary as a feature of portable fuel gas conditioning system 625. When optionally employed, pumps may be a vacuum pumps and/or fluid-differential pressure pumps. For net differential pressure, a centrifugal pump may be beneficial because the impeller imparts energy to result in a discharge pressure.

Time Increments

Turning now to FIGS. 3A-3L, the twelve Time Increments shown in row 260 of FIG. 2 will now be described. Although each bed undergoes seven steps in the cycle of illustrative embodiments, the seven steps of the cycle may not be of equal length of time. Therefore, it may be advantageous for the reader's understanding to break the cycle into twelve Time Increments to illustrate the interaction between the beds, as shown in FIGS. 3A-3L. Prior to Time Increment 1, the four-bed system may be primed and a few cycles taken to reach a periodic state. FIGS. 3A-3L assume a periodic state has been reached. Each Time Increment may be conducted for a period of from a few seconds to a few minutes, depending on the flow rate and composition of feed gas 105. In one illustrative example, "x" in row 240 of FIG. 2 may be 40 seconds, for a total cycle time of 960 seconds (16 minutes). In another illustrative example, "x" may be 160 seconds for a total cycle time of 24 minutes. The ability to change the duration of the CoD step 140 and CnD 150 steps independently of each other to extend the cycle time without impacting the equalization timesteps, allows the method to trade-off the purity and recovery of fuel gas 860 product, based on feed gas 105 composition. In embodiments where no buffer tank 165 is employed, "x" may be zero and the duration of CoD step 140 may be the same as the LR step 160. In the particular case of fuel gas 860, recovery may be sacrificed for sufficient purity to obtain high-quality fuel gas and/or sufficiently high Methane Number, because any separated heavier hydrocarbons 205 and/or any unseparated methane may be recirculated back into the gas gathering system.

FIG. 3A illustrates Time Increment 1 of FIG. 2. At Time Increment 1, Bed A may be undergoing feed step 100, with heated, pressurized feed gas 105 entering Bed A, and fuel gas 860 being collected from Bed A. Feed gas may be heated to at least 100° C. and be pressurized from wellhead 815 and/or from a compressor inherent in the field such as single-stage compressor 845 or multi-stage compressor 850. Simultaneously, Bed B may be undergoing EqD step 130. Pressurized gas 305 flows from Bed B to Bed D to reduce the pressure in Bed B and simultaneously increase the pressure in Bed D. Bed C may be undergoing CnD step 150 in which separated heavier hydrocarbons 205 and any unrecovered methane may be removed from Bed C and recirculated to rich gas discharge line 830 and/or the gas gathering system.

At Time Increment 2 shown in FIG. 3B, Bed A is still undergoing feed step 100, but portion 115 of fuel gas 860 is now diverted to Bed D, which is undergoing FGP step 180. Bed B has progressed to CoD step 140, with purge gas 155 from Bed B being stored in buffer tank 165. Bed C continues with CnD step 150.

FIG. 3C illustrates Time Increment 3, where Bed A continues with feed step 100 while providing portion 115 of fuel gas 860 to re-pressurize Bed D which may be undergoing FGP step 180. Bed B continues with CoD step 140, providing purge gas 155 to buffer tank 165. Bed C progresses to LR Step 160. Purge gas 155 flows through Bed C in a countercurrent so that separated heavier hydrocarbons 205 may be removed from the feed end 125 of Bed C and recirculated to rich gas discharge line 830.

Figure 3D:
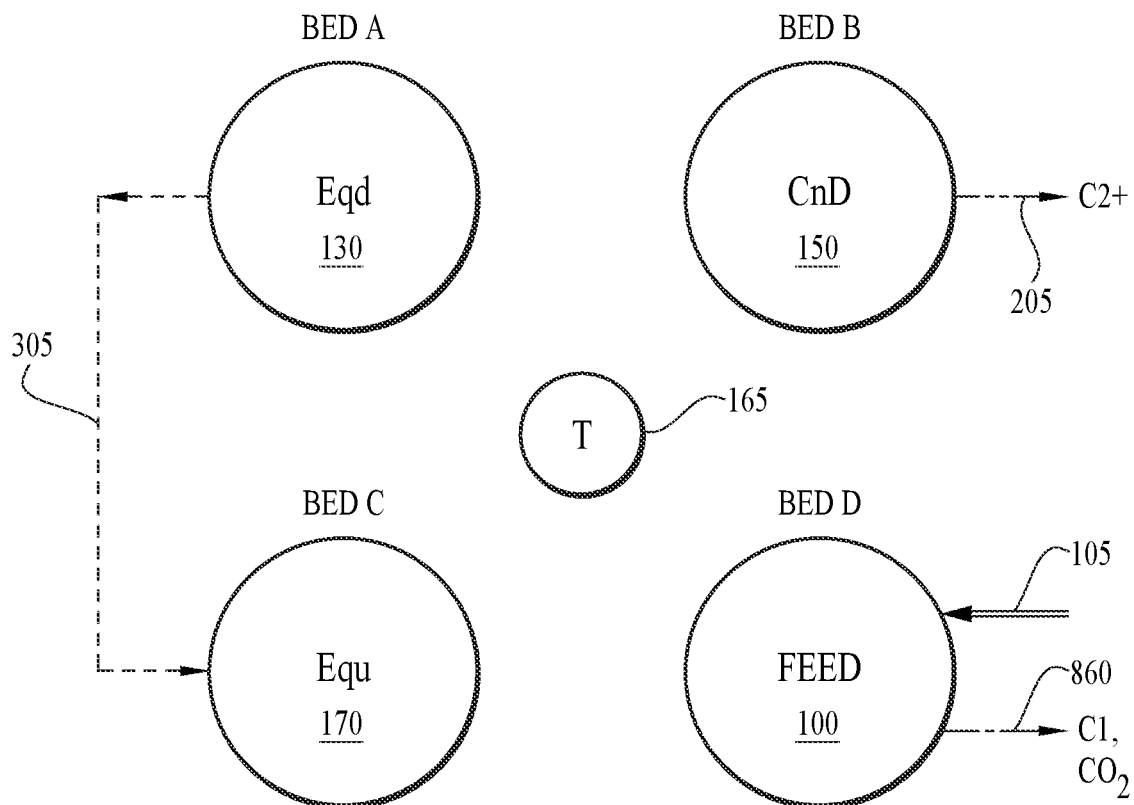

As shown in FIG. 3D, during Time Increment 4, Bed A has now begun EqD step 130, providing pressurized gas 305 to Bed C in order to begin re-pressurizing Bed C, which Bed C has begun EqU step 170. Bed B initiates CnD step 150 producing gaseous separated heavier hydrocarbons 205 from the feed end 125 of Bed B back to rich gas discharge line 830. Bed D begins feed step 100, accepting heated, pressurized feed gas 105 and producing fuel gas 860 from the product end 135 of Bed D.

Figure 3E:
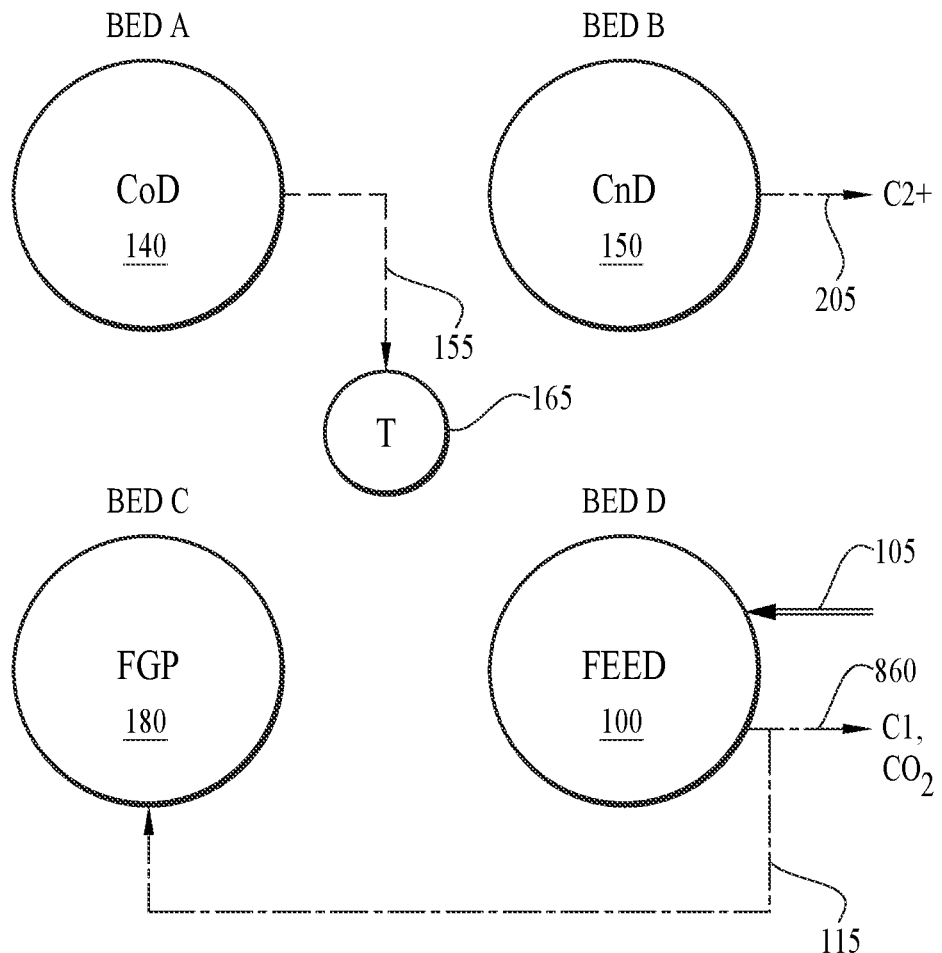

Turning to FIG. 3E, at Time Increment 5, Bed C cycles to FGP step 180. Bed D continues to undergo feed step 100, and a portion 115 of fuel gas 860 produced from Bed D is diverted to Bed C to re-pressurize Bed D back to the initial cycle pressure of 100-150 psia, for example or 50-210 psia. Bed A, moves to CoD step 140, sending purge gas 155 to buffer tank 165. Bed B continues with CnD step 150, producing separated heavier hydrocarbons 205 and any unseparated methane back to rich gas discharge line 830 and/or the gas gathering system.

Figure 3F:
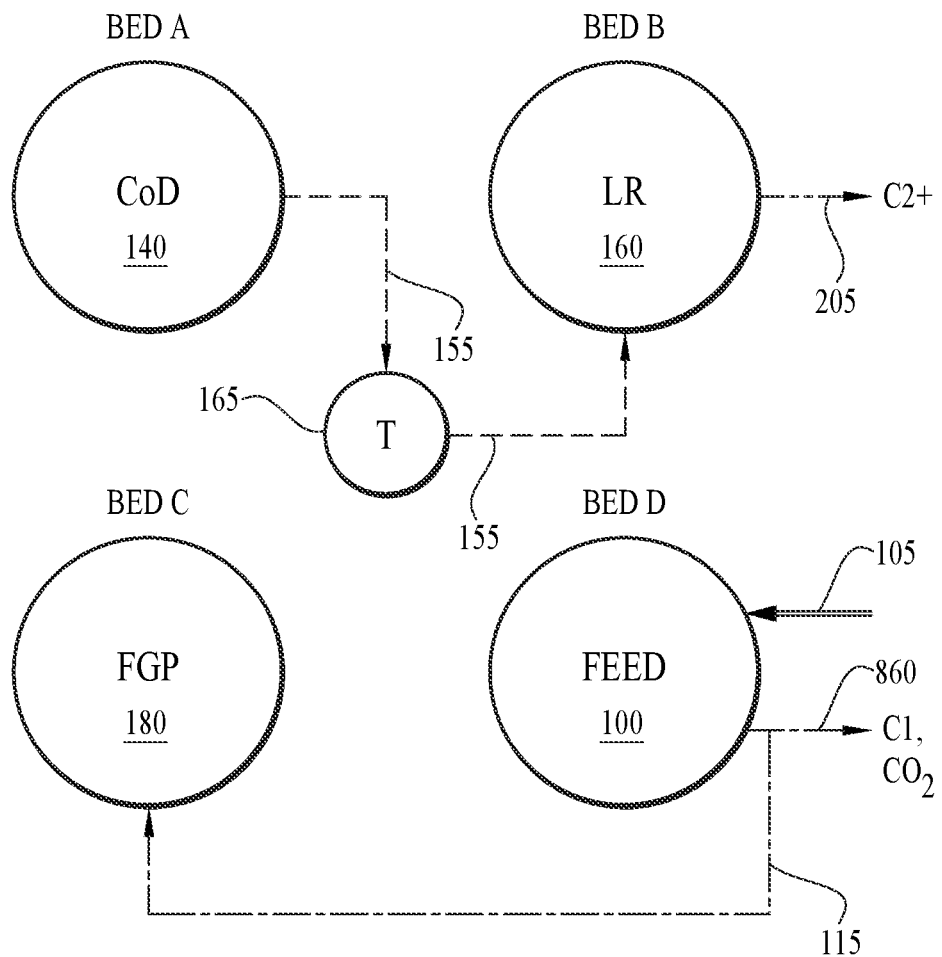

At Time Increment 6 as shown in FIG. 3F, Bed D is still undergoing feed step 100, and portion 115 of fuel gas 860 continues to be diverted to Bed C, which is still undergoing FGP step 180. Bed A continues in CoD step 140, supplying purge gas 155 to buffer tank 165. At Time Increment 6, purge gas 155 from buffer tank 165 flushes in a countercurrent through Bed B, which Bed B has cycled to LR step 160. Simultaneously, while purge gas 155 flows through Bed B in a countercurrent, separated heavier hydrocarbons 205 are withdrawn from the feed end 125 of Bed B.

During Time Increment 7, as shown in FIG. 3G, Bed D progresses to EqD step 130, supplying pressurized gas 305 to Bed B, which has begun EqU step 170. At Time Increment 7 Bed A is undergoing CnD step 150, and Bed C has begun feed step 100. Purge gas 155 no longer flows from Bed A to buffer tank 165 nor from buffer tank 165 to Bed B.

Figure 3H:
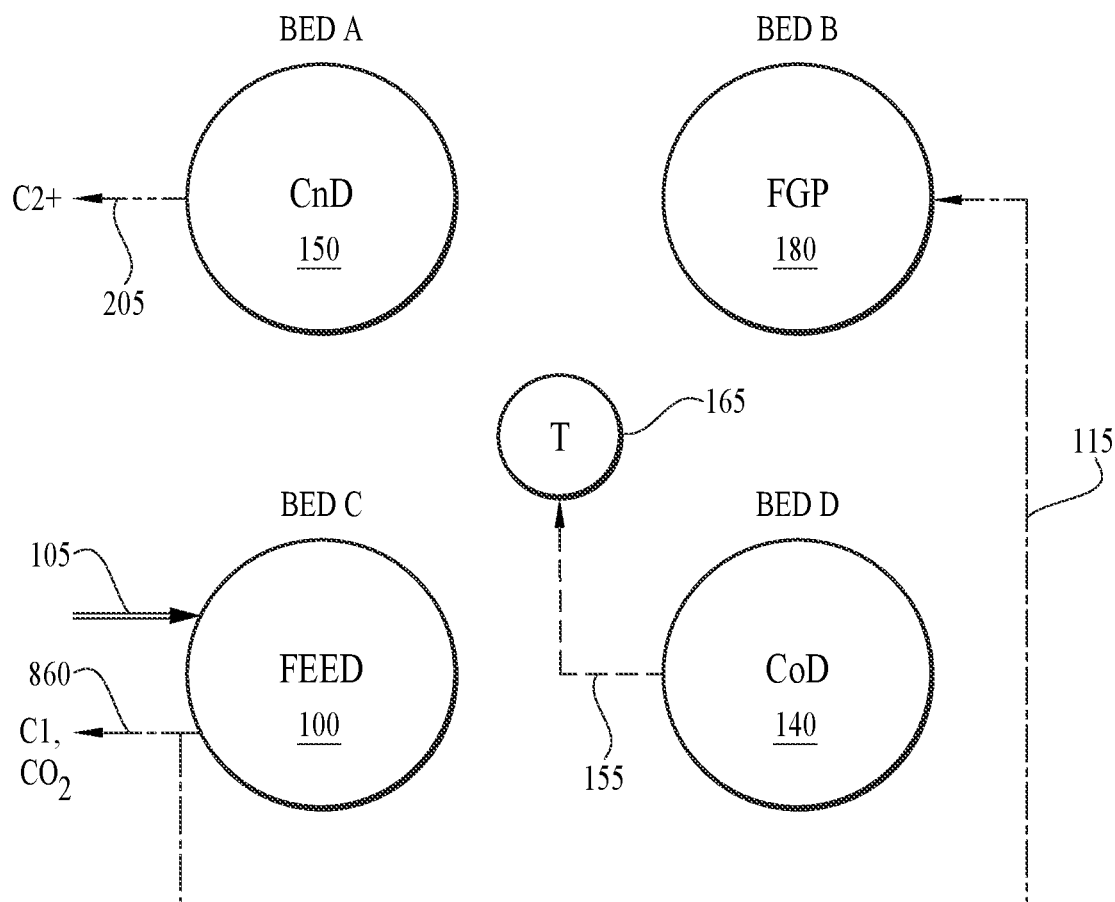

At Time Increment 8 as shown in FIG. 3H, Bed C is still undergoing feed step 100, but portion 115 of fuel gas 860 is now diverted to Bed B, which is undergoing FGP step 180. Bed D has progressed to CoD step 140, with purge gas 155 from Bed B being stored in buffer tank 165. Bed A continues with CnD step 150.

FIG. 3I illustrates Time Increment 9. Now Bed C continues with feed step 100 while providing portion 115 of fuel gas 860 to re-pressurize Bed B undergoing FGP step 180. Bed D continues with CoD step 140 providing purge gas 155 to buffer tank 165. Bed A progresses to LR Step 160. Purge gas 155 flows through Bed A in a countercurrent and separated heavier hydrocarbons 205 may be removed from the feed end 125 of Bed A and recirculated to rich gas discharge line 830.

As shown in FIG. 3J, during Time Increment 10 Bed C has now begun EqD step 130, providing pressurized gas 305 to Bed A in order to begin re-pressurizing Bed A. At the same time, Bed A has begun EqU step 170. Bed D initiates CnD step 150 producing gaseous separated heavier hydrocarbons 205 from the feed end 125 of Bed D back to rich gas discharge line 830. Bed B begins feed step 100, accepting heated, pressurized feed gas 105 and producing fuel gas 860 from the product end 135 of Bed B.

Figure 3K:
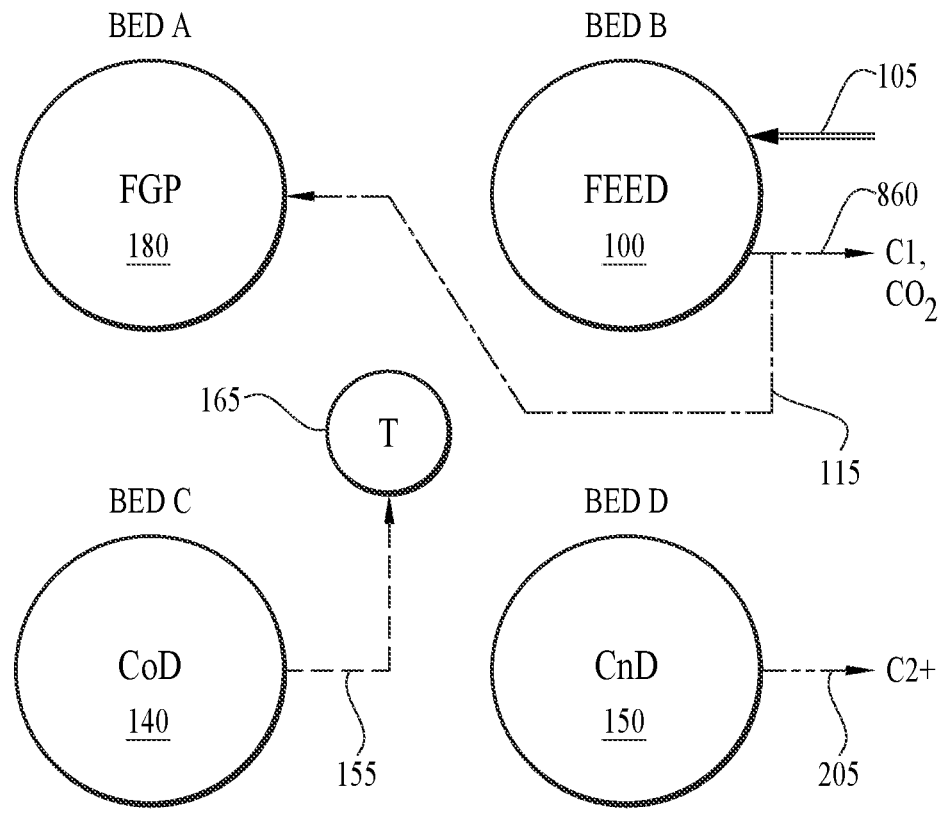

Turning to FIG. 3K, at Time Increment 11 Bed A cycles to FGP step 180. Bed B continues to undergo feed step 100, and a portion 115 of fuel gas 860 produced from Bed B is diverted to Bed A to repressurize Bed A back to the initial cycle pressure which may, for example, be 100-150 psia, or 50-210 psia. Bed C, moves to CoD step 140, sending purge gas 155 to buffer tank 165. Bed D continues with CnD step 150, producing separated heavier hydrocarbons 205 and any unseparated methane back to rich gas discharge line 830 and/or the gas gathering system.

Figure 3L:
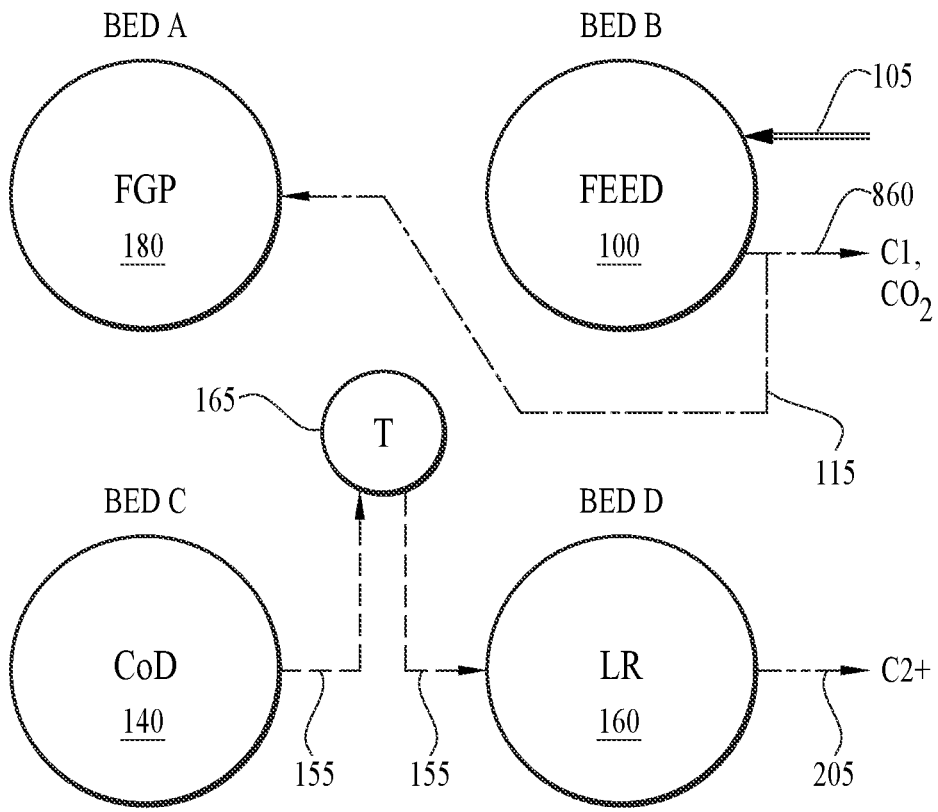

At Time Increment 12 as shown in FIG. 3L, Bed B is still undergoing feed step 100, and portion 115 of fuel gas 860 continues to be diverted to Bed A, which is still undergoing FGP step 180. Bed C continues in CoD step 140, supplying purge gas 155 to buffer tank 165. Also at Time Increment 12, purge gas 155 from buffer tank 165 flushes in a countercurrent through Bed D, which Bed D has cycled to LR step 160. Simultaneously, while purge gas 155 flows through Bed D, separated heavier hydrocarbons 205 are withdrawn from the feed end 125 of Bed D.

Some or all-time increments may be repeated, extended or reduced as needed or desired. In embodiments where buffer tank 165 is omitted, the length of CoD step 140 and LR step 160 may be the same. Those of skill in the art may appreciate the number of beds and steps may be increased or decreased depending on the number of equalization steps desired. Additional equalization steps may allow for handling of feed gas 105 of more varied compositions.

Pressure Swing Adsorption (PSA) Examples

The following examples demonstrate that the PSA cycle for fuel gas conditioning of illustrative embodiments may be adaptable and robust for wellsite and field use over a range of gas compositions. Unlike conventional methods, illustrative embodiments may address the variability of feed gas compositions that would typically be encountered in different geographical locations and geological formations. The following examples employ the exemplary feed gas compositions set forth in Table 2.

TABLE 2

Exemplary Feed Gas Compositions

| Composition, mol % | Low BTU | Medium BTU | High BTU |
|---|---|---|---|
| $CO_2$ | 0.50 | 2.22 | 0.80 |
| C1 | 82.10 | 62.45 | 43.60 |
| C2 | 10.90 | 16.87 | 28.80 |
| C3 | 4.30 | 13.48 | 18.50 |
| C4 | 1.50 | 3.71 | 6.60 |
| C5 | 0.50 | 0.93 | 1.40 |
| C6 | 0.20 | 0.34 | 0.30 |
| Total | 100 | 100 | 100 |
| Gross Heating Value (BTU/scf) | 1,200 | 1,440 | 1,700 |

Example 1 considers application of PSA system 820 and/or fuel gas conditioning system 625 of illustrative embodiments handling the "Medium BTU" raw natural gas stream as feed gas 105, with initial feed pressure of 150 psia for fuel gas conditioning purposes. The separation and recovery may follow the cycle and schedule of illustrative embodiments herein, and the results are illustrated in Table 3.

TABLE 3

Fuel Gas Product and Separated Heavier Hydrocarbons for Example 1

| | Fuel Gas Product | | Separated Heavier Hydrocarbons | |
|---|---|---|---|---|
| Composition | Recovery % | Mol % | Recovery % | Mol % |
| $CO_2$ | 77.2 | 2.6 | 22.8 | 1.4 |
| C1 | 88.8 | 87.8 | 11.2 | 18.9 |
| C2 | 26.1 | 7.1 | 73.9 | 33.8 |
| C3 | 11.0 | 2.4 | 89.1 | 32.6 |
| C4 | 1.5 | 0.1 | 98.7 | 10.0 |
| C5 | 0.0 | 0.0 | 100.0 | 2.4 |
| C6 | 0.0 | 0.0 | 100.0 | 0.9 |
| Total | | 100 | | 100 |
| Gross Heating Value (BTU/scf) | | 1,069 | | |
| Methane Number (MN) | | 80 | | |

Table 3 shows the production of fuel gas 860 that may be good quality fuel that meets engine manufacturer specifications and high Methane Number to allow for optimal operation of engines used for compression purposes and for power generation equipment, for example for single-stage compressor 845, multi-stage compressor 850 and/or micro-grid 840.

The purpose of fuel gas conditioning may be to take only a slipstream of raw gas 835 and/or unprocessed gas (such as rich gas 870) and condition it for combustion purposes. The separated heavier hydrocarbons 205 may be returned to the inlet scrubber of multi-stage compressor 850 for processing further downstream at a centralized gas processing facility, as for example shown in FIG. 5A. Because separated heavier hydrocarbons 205 may be recovered and returned to the gathering and/or transport system, the higher value hydrocarbons and even the methane in separated heavier hydrocarbons 205 may, in some embodiments, be monetized downstream and not wasted or combusted. Hence, PSA system 820 may eliminate the need to maximize methane recovery for fuel gas 860 purposes, because any methane not separated for fuel gas 860 purposes may be returned to the gathering system.

In Example 2, when raw gas 835, rich gas 870 and/or feed gas 105 is richer, such as in the "higher BTU" case in Table 2, the same four-bed seven-step method for adsorption for fuel gas conditioning may be used. At the same feed flowrate and pressure, a high-quality fuel gas 860 methane product may be produced by reducing the duration of countercurrent depressurization step 150 and/or by decreasing the cycle time, with the results as shown in Table 4. Once more, high recovery of heavier hydrocarbons is achieved by these methods, meaning that high-quality fuel gas can be achieved, simply by adjusting cycle time of the method. The richer the incoming raw gas 835 and/or rich gas 870 to the system, the shorter the cycle time may be, without adversely impacting the quality of fuel gas 860 created. The results of Example 2 are illustrated in Table 4.

TABLE 4

Fuel Gas Product and Separated Heavier hydrocarbons for Example 2

| | Fuel Gas Product | | Separated Heavier Hydrocarbons | |
|---|---|---|---|---|
| Composition | Recovery % | Mol % | Recovery % | Mol % |
| $CO_2$ | 75.1 | 1.5 | 24.9 | 0.3 |
| C1 | 84.3 | 87.7 | 15.8 | 11.8 |
| C2 | 13.0 | 9.5 | 87.2 | 42.9 |

TABLE 4-continued

Fuel Gas Product and Separated Heavier hydrocarbons for Example 2

| Composition | Fuel Gas Product | | Separated Heavier Hydrocarbons | |
|---|---|---|---|---|
| | Recovery % | Mol % | Recovery % | Mol % |
| C3 | 2.7 | 1.2 | 97.4 | 30.8 |
| C4 | 0.2 | .1 | 99.8 | 11.3 |
| C5 | 0.0 | 0.0 | 100.0 | 2.4 |
| C6 | 0.0 | 0.0 | 100.0 | 0.5 |
| Total | | 100 | | 100 |
| Gross Heating Value (BTU/scf) | | 1,077 | | |
| Methane Number (MN) | | 78 | | |

In Example 3, a PSA process without a buffer tank is employed to process the "Medium BTU" rich gas 870 at an initial feed pressure of 150 psia. In this example, the process sequence of Table 5 for a four-bed seven-step PSA method and/or process may be employed, as follows:

TABLE 5

Process Sequence and Schedule for a 4-bed and 7-step PSA System

| Bed1 | Feed | | Eqd | CoD | CnD | LR | Equ | FGP | | |
|---|---|---|---|---|---|---|---|---|---|---|
| Bed2 | Eqd | CoD | CnD | LR | Equ | FGP | | Feed | | |
| Bed3 | CnD | LR | Equ | FGP | | Feed | | Eqd | CoD | |
| Bed4 | Equ | FGP | | Feed | | Eqd | CoD | CnD | LR | |
| Time,s | y | z | y | z | y | z | y | z | | |

The shortening of CnD step 150 and direct coupling of CoD step 140 with LR step 160 may allow the PSA cycle times to be further reduced without impacting fuel gas conditioning performance. The embodiment of Table 5 may allow for greater throughput capacity of the system without increasing adsorber vessel (bed) sizes or PSA system 820 and/or fuel gas conditioning system 625 footprint. This may be a significant improvement, especially when the goal is the portable, compact fuel gas conditioning system 625 of illustrative embodiments. In the embodiment of Table 5, a high-quality fuel gas with a gross heating value of less than 1,100 Btu/scf is produced at a higher flowrate, such as a flow rate of 750,000 scfd to 1,000,000 scfd. Table 6 illustrates the results of Example 3 of illustrative embodiments.

TABLE 6

Fuel Gas Product and Separated Heavier Hydrocarbons for Example 3

| Composition | Fuel Gas Product | | Separated Heavier Hydrocarbons | |
|---|---|---|---|---|
| | Recovery % | Mol % | Recovery % | Mol % |
| CO$_2$ | 65.5 | 2.4 | 34.6 | 1.9 |
| C1 | 83.8 | 88.0 | 16.1 | 24.9 |
| C2 | 29.2 | 8.4 | 70.1 | 29.4 |
| C3 | 4.8 | 1.2 | 95.2 | 31.6 |
| C4 | 0.0 | 0.0 | 100.0 | 9.2 |
| C5 | 0.0 | 0.0 | 100.0 | 2.1 |
| C6 | 0.0 | 0.0 | 100.0 | 0.9 |
| Total | | 100 | | 100 |
| Gross Heating Value (BTU/scf) | | 1,067 | | |
| Methane Number (MN) | | 80 | | |

Turning to Example 4, when rich gas 870 and/or feed gas 105 is relatively richer, such as in the "Higher BTU" case in Table 2, a four-bed, seven-step adsorption for fuel gas conditioning without buffer tank 165 is illustrated. At the faster feed flowrates and same 150 psia feed pressure, a high-quality high-methane fuel gas 860 may be produced by reducing the time for CnD step 150 and CoD step 140, which may lead to a decrease in the overall cycle time, with the results shown in Table 7. Similar to previous examples, high recovery of separated heavier hydrocarbons 205 is achieved by this method, meaning that high-quality fuel gas 860 may be achieved by reducing the cycle time of the process. The richer the incoming feed gas 105, the faster the cycle time.

TABLE 7

Fuel Gas Product and Separated Heavier Hydrocarbons for Example 4

| Composition | Fuel Gas Product | | Separated Heavier Hydrocarbons | |
|---|---|---|---|---|
| | Recovery % | Mol % | Recovery % | Mol % |
| CO$_2$ | 59.7 | 1.2 | 40.3 | 0.5 |
| C1 | 81.2 | 86.1 | 18.8 | 14.0 |
| C2 | 18.3 | 12.1 | 81.5 | 40.1 |
| C3 | 1.5 | 0.6 | 98.5 | 31.1 |
| C4 | 0.0 | 0.0 | 100.0 | 11.3 |
| C5 | 0.0 | 0.0 | 100.0 | 2.4 |
| C6 | 0.0 | 0.0 | 100.0 | 0.6 |
| Total | | 100 | | 100 |
| Gross Heating Value (BTU/scf) | | 1,096 | | |
| Methane Number (MN) | | 77 | | |

A portable pressure swing adsorption method and system for fuel gas conditioning has been described. Further modifications and alternative embodiments of various aspects of the invention may be apparent to those skilled in the art in view of this description. Accordingly, this description is to be construed as illustrative only and is for the purpose of teaching those skilled in the art the general manner of executing the invention. It is to be understood that the forms of the invention shown and described herein are to be taken as the presently preferred embodiments. Elements and materials may be substituted for those illustrated and described herein, parts and processes, methods may be reversed, and certain features of the invention may be utilized independently, all as would be apparent to one skilled in the art after having the benefit of this description of the invention. Changes may be made in the elements described herein without departing from the scope and range of equivalents as described in the following claims. In addition, it is to be understood that features described herein independently may, in certain embodiments, be combined.

What is claimed is:
1. A fuel gas conditioning method, comprising:
   connecting a fuel gas conditioning system to a rich gas stream discharged one of from a first stage of compression, from a single-stage compressor, at 50-215 psia, or a combination thereof, wherein the fuel gas conditioning system comprises a pressure swing adsorption (PSA) system;
   heating at least a portion of the rich gas stream to at least 100° C.;
   accepting the heated at least the portion of the rich gas stream as feed gas into the fuel gas conditioning system;
   flowing the feed gas through the PSA system, wherein the PSA system adsorbs at least a portion of ethane-plus

(C2+) hydrocarbons from the feed gas to produce a high-quality fuel gas;

fluidly coupling the high-quality fuel gas to a fuel line;

adiabatically at at least 100° C. lowering the pressure of the adsorbent bed to desorb the at least the portion of C2+ hydrocarbons, wherein the portion of C2+ hydrocarbons so desorbed are in gaseous form; and returning the gaseous at least the portion of C2+ hydrocarbons to one of the rich gas stream, a raw gas stream or a gas gathering system.

2. The fuel gas conditioning method of claim 1, wherein the rich gas stream is discharged at 50-215 psia.

3. The fuel gas conditioning method of claim 1, wherein the PSA system comprises a plurality of adsorbent beds, and wherein a first adsorbent bed of the plurality of adsorbent beds produces the high-quality fuel gas during a same time increment as a second adsorbent bed of the plurality of adsorbent beds produces the desorbed C2+ hydrocarbons.

4. The fuel gas conditioning method of claim 3, wherein a product end of the first adsorbent bed discharges the high-quality fuel gas and a feed end of the second adsorbent bed returns the gaseous C2+ hydrocarbons to the one of the rich gas stream, the raw gas stream or the gas gathering system.

5. The fuel gas conditioning method of claim 3, wherein upon conclusion of the time increment, the first adsorbent bed transfers pressurized gas to the second adsorbent bed.

6. The fuel gas conditioning method of claim 3, wherein the PSA system further comprises a buffer tank, the buffer tank fluidly coupling a purge gas between a third bed of the plurality of adsorbent beds and the second adsorbent bed.

7. The fuel gas conditioning method of claim 3, wherein a portion of the fuel gas is diverted to an adsorbent bed of the plurality of adsorbent beds undergoing a fuel gas pressurization (FGP) step, the diverted fuel gas re-pressurizing the adsorbent bed undergoing the FGP step.

8. The fuel gas conditioning method of claim 1, wherein the high-quality fuel gas flowing through the fuel line powers an engine in the gas gathering system.

9. The fuel gas conditioning method of claim 1, wherein the fuel gas conditioning system is portable.

10. The fuel gas conditioning method of claim 1, wherein the PSA system comprises four adsorbent beds and cycles through seven steps in an adsorption and desorption cycle.

* * * * *